United States Patent
Kehne et al.

(10) Patent No.: US 8,188,009 B2
(45) Date of Patent: May 29, 2012

(54) 4-(3-AMINOBENZOYL)-5-CYCLOPROPYLISOXAZOLES EFFECTIVE AS HERBICIDES

(75) Inventors: Heinz Kehne, Hofheim (DE); Andreas Almsick, Karben (DE); Hartmut Ahrens, Egelsbach (DE); Dieter Feucht, Eschborn (DE); Ines Heinemann, Hofheim (DE); Jan Dittgen, Frankfurt (DE); Martin Jeffrey Hills, Idstein (DE); Stefan Lehr, Liederbach (DE); Christopher Hugh Rosinger, Hofheim (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 12/920,805

(22) PCT Filed: Mar. 19, 2009

(86) PCT No.: PCT/EP2009/002029
§ 371 (c)(1),
(2), (4) Date: Sep. 2, 2010

(87) PCT Pub. No.: WO2009/118125
PCT Pub. Date: Oct. 1, 2009

(65) Prior Publication Data
US 2011/0015073 A1    Jan. 20, 2011

(30) Foreign Application Priority Data
Mar. 26, 2008 (EP) .................................. 08005632

(51) Int. Cl.
*A01N 43/80* (2006.01)
*C07D 261/12* (2006.01)
(52) U.S. Cl. ........................ 504/271; 548/248
(58) Field of Classification Search .............. None
See application file for complete search history.

(56) References Cited

U.S. PATENT DOCUMENTS

| | | |
|---|---|---|
| 4,173,650 A | 11/1979 | Hanfin |
| 2005/0288516 A1 | 12/2005 | Warren |
| 2006/0240984 A1 * | 10/2006 | Pallett et al. .................. 504/103 |

FOREIGN PATENT DOCUMENTS

| | | | |
|---|---|---|---|
| EP | 0418175 | | 3/1991 |
| EP | 0527036 | | 2/1993 |
| EP | 0636622 | | 2/1995 |
| WO | WO 95/16678 | * | 6/1995 |
| WO | WO 95/22903 | * | 8/1995 |
| WO | 97/30037 | | 8/1997 |
| WO | WO 97/30037 | * | 8/1997 |
| WO | 98/51153 | | 11/1998 |

OTHER PUBLICATIONS

International Search Report based on PCT/EP2009/002029 dated Jun. 15, 2009.

* cited by examiner

*Primary Examiner* — Joseph K. McKane
*Assistant Examiner* — Alicia L Otton
(74) *Attorney, Agent, or Firm* — Baker Donelson Bearman, Caldwell & Berkowitz, PC

(57) ABSTRACT

4-(3-Aminobenzoyl)-5-cyclopropylisoxazoles of the formula (I) are described as herbicides.

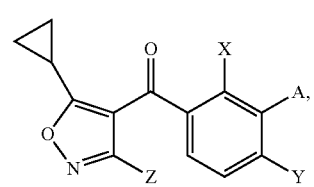

In this formula (I), A, X, Y and Z are radicals such as hydrogen, organic radicals such as alkyl, and other radicals such as halogen.

16 Claims, No Drawings

4-(3-AMINOBENZOYL)-5-CYCLOPROPYLISOXAZOLES EFFECTIVE AS HERBICIDES

CROSS REFERENCE TO RELATED APPLICATIONS

This application is a §371 National Stage Application of PCT/EP2009/002029 filed Mar. 19, 2009, which claims priority to European Application No. 08005632.8 filed Mar. 26, 2008.

BACKGROUND OF THE INVENTION

1. Field of the Invention

The invention relates to the technical field of the herbicides, in particular to that of the herbicides for the selective control of broad-leafed leaves and grass weeds in crops of useful plants.

2. Description of Related Art

It has already been disclosed in various publications that certain benzoylisoxazoles have herbicidal properties. Thus, EP 0 418 175, EP 0 527 036 and WO 97/30037 describe benzoylisoxazoles which are substituted on the phenyl ring by a variety of radicals.

However, the compounds known from these publications frequently do not display a sufficient herbicidal activity. It is therefore an object of the present invention to provide herbicidally active compounds whose herbicidal properties are improved over those of the compounds known from the prior art.

SUMMARY OF THE INVENTION

It has now been found that certain 4-benzoylisoxazoles which have a cyclopropyl group attached in the 5-position and whose phenyl ring has an amino or amidine group attached in the 3-position are especially suitable as herbicides.

The present invention relates to 4-(3-aminobenzoyl)-5-cyclopropylisoxazoles of the formula (I) or their salts (I)

in which
A is $NR^1R^2$ or $N=CR^3NR^4R^5$,
$R^1$ and $R^2$ independently of one another are hydrogen, ($C_1$-$C_6$)-alkyl, ($C_1$-$C_4$)-alkoxy-($C_1$-$C_6$)-alkyl, ($C_2$-$C_6$)-alkenyl, ($C_2$-$C_6$)-alkynyl, ($C_3$-$C_6$)-cycloalkyl or ($C_3$-$C_6$)-cycloalkyl-($C_1$-$C_6$)-alkyl, where the six abovementioned radicals are substituted by m halogen atoms,
$R^3$, $R^4$ and $R^5$ independently of one another are hydrogen, ($C_1$-$C_6$)-alkyl or ($C_3$-$C_6$)-cycloalkyl, where the three last-mentioned radicals are substituted by m halogen atoms,
X and Y independently of one another are hydrogen, ($C_1$-$C_6$)-alkyl, ($C_1$-$C_4$)-alkoxy, ($C_1$-$C_4$)-alkoxy-($C_1$-$C_6$)-alkyl, ($C_2$-$C_6$)-alkenyl, ($C_2$-$C_6$)-alkynyl, ($C_3$-$C_6$)-cycloalkyl, ($C_3$-$C_6$)-cycloalkyl-($C_1$-$C_6$)-alkyl, ($C_1$-$C_6$)-haloalkyl, halogen, ($C_1$-$C_4$)-alkyl-S(O)$_n$, ($C_3$-$C_6$)-cycloalkyl-S(O)$_n$, nitro or cyano,
Z is hydrogen or $CO_2R^6$,
$R^6$ is ($C_1$-$C_6$)-alkyl or ($C_3$-$C_6$)-cycloalkyl,
m is 0, 1, 2, 3, 4 or 5,
n is 0, 1 or 2.

DETAILED DESCRIPTION OF A PREFERRED EMBODIMENT

In formula (I) and all formula given below, alkyl radicals which have more than two carbon atoms may be straight-chain or branched. Alkyl radicals are, for example, methyl, ethyl, n- or i-propyl, n-, i-, t- or 2-butyl, pentyls, hexyls, such as n-hexyl, i-hexyl and 1,3-dimethylbutyl. Halogen is fluorine, chlorine, bromine or iodine.

If a group is polysubstituted by radicals, this is to be understood as meaning that this group is substituted by one or more of the abovementioned radicals which are identical or different.

Depending on the nature and linkage of the substituents, the compounds of the formula (I) may be present in the form of stereoisomers. If, for example, one or more asymmetric carbon atoms are present, enantiomers and diastereomers may occur. Equally, stereoisomers occur when n is 1 (sulfoxides). Stereoisomers can be obtained from the mixtures generated in the course of the preparation by customary separation methods, for example by chromatographic separation methods. Equally, stereoisomers can be prepared selectively using stereoselective reactions and employing optically active starting materials and/or adjuvants. The invention also relates to all stereoisomers and their mixtures which are comprised by the formula (I), but are not specifically defined.

Preferred compounds of the formula (I) are those in which
A is $NR^1R^2$ or $N=CR^3NR^4R^5$,
$R^1$ and $R^2$ independently of one another are hydrogen, ($C_1$-$C_6$)-alkyl, ($C_1$-$C_4$)-alkoxy-($C_1$-$C_6$)-alkyl, ($C_2$-$C_6$)-alkenyl, ($C_3$-$C_6$)-cycloalkyl or ($C_3$-$C_6$)-cycloalkyl-($C_1$-$C_6$)-alkyl,
$R^3$, $R^4$, $R^5$ independently of one another are hydrogen or ($C_1$-$C_6$)-alkyl,
X and Y independently of one another are methyl, methoxy, trifluoromethyl, chlorine, bromine, fluorine or methylsulfonyl,
Z is hydrogen or $CO_2R^6$,
$R^6$ is methyl or ethyl.

Especially preferred compounds of the formula (I) are those in which
A is $NR^1R^2$ or $N=CR^3NR^4R^5$,
$R^1$ and $R^2$ independently of one another are hydrogen, methyl, ethyl, propyl, methoxyethyl, ethoxyethyl or methoxypropyl,
$R^3$, $R^4$, $R^5$ independently of one another are hydrogen or methyl,
X and Y independently of one another are methyl, methoxy, trifluoromethyl, chlorine, bromine, fluorine or methylsulfonyl,
Z is hydrogen or $CO_2R^6$,
$R^6$ is methyl or ethyl.

Unless otherwise defined, the substituents and symbols in all the formulae mentioned hereinbelow have the same meaning as described in formula (I).

For example, compounds according to the invention in which Z is hydrogen can be prepared by the method specified in Scheme 1 and known from EP 0 418 175 A1 by reacting a compound of the formula (II) with a salt of hydroxylamine, such as hydroxylamine hydrochloride, in a suitable solvent such as ethanol or acetonitrile, if appropriate with catalysis of a base such as triethylamine, at a temperature of from room temperature up to the temperature of the boiling point of the solvent. In formula (II), L is a group such as ethoxy or dimethylamino.

by reacting a compound of the formula (IIa) with hydroxylamine or a salt thereof in a suitable solvent such as ethanol or acetonitrile, if appropriate with catalysis of a base such as triethylamine, at a temperature of from room temperature up to the temperature of the boiling point of the solvent.

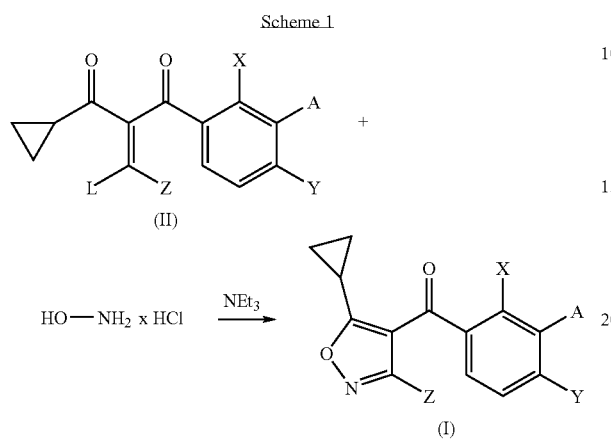

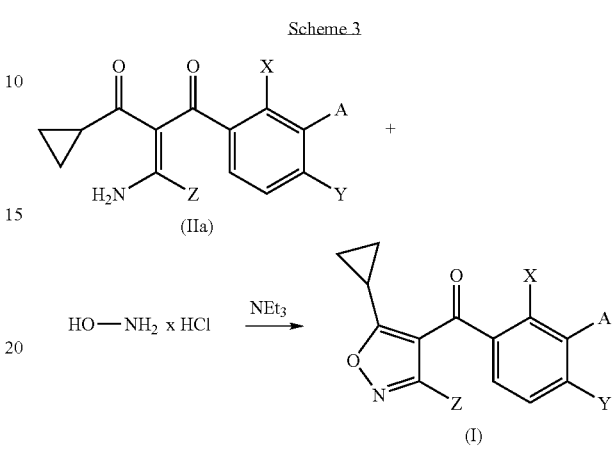

Compounds of the formula (II) can be prepared for example by the method specified in Scheme 2 and in J. Heterocyclic Chem., 1976, 13, 973 by reacting the dione (III) with, for example, triethyl orthoformate with acid catalysis.

Compounds according to the invention in which Z is $CO_2R^6$ can also be prepared for example by the method specified in Scheme 4 and known from WO 98/5153 by reacting a compound of the formula (III) with a 2-chloro-2-hydroxyiminoacetic ester of the formula (V).

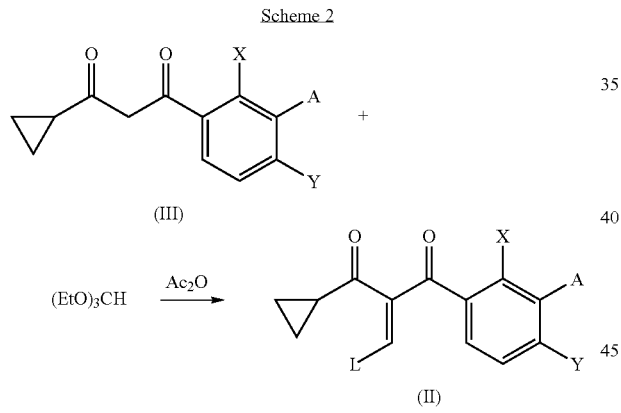

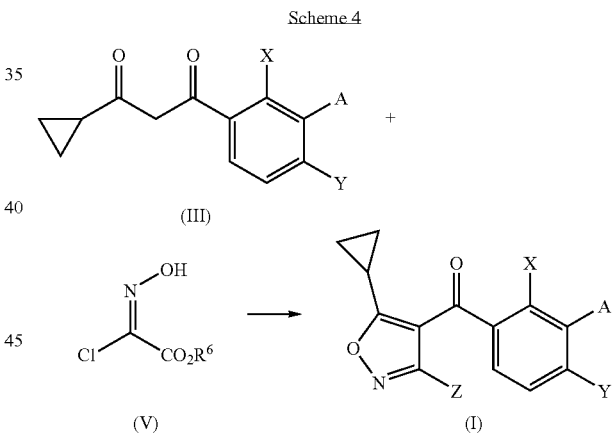

The preparation of compounds of the formula (III) is known to the skilled worker in principle and can be effected for example with trisubstituted benzoic acids of the formula (IV) or their derivatives such as acid chloride or ester. For example, such benzoic acids of the formula (IV) can be prepared by the methods described in WO 98/42678.

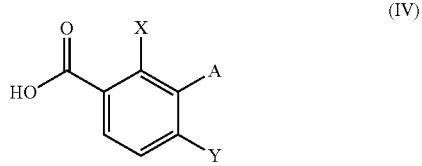

Compounds according to the invention in which Z is hydrogen or $CO_2R^6$ can be prepared for example by the method specified in Scheme 3 and known from WO 97/30037

Compounds of the formulae (II) and (IIa) in which X, Y, A and Z are defined as for formula (I) and L is defined as mentioned above are novel and also subject matter of the present application.

Collections of compounds of the formula (I) and/or their salts which can be synthetized in accordance with the above-mentioned reactions can also be prepared in a parallelized manner, which can be effected manually or in a partly or fully automated manner. Here, it is possible for example to automate the procedure of the reaction, the work-up or the purification of the products or intermediates. In total, this is understood as meaning the procedure as described for example by D. Tiebes in Combinatorial Chemistry—Synthesis, Analysis, Screening (Editor Günther Jung), Wiley 1999, on pages 1 to 34.

A series of commercially available apparatuses can be used for the parallelized reaction procedure and work-up, for example Calpyso reaction blocks from Barnstead International, Dubuque, Iowa 52004-0797, USA, or reaction stations from Radleys, Shirehill, Saffron Walden, Essex, CB 11 3AZ, England or MultiPROBE Automated Workstations from Perkin Elmar, Waltham, Mass. 02451, USA. Chromatographic apparatuses, for example from ISCO, Inc., 4700 Superior Street, Lincoln, Nebr. 68504, USA, are available, inter alia, for the parallelized purification of compounds of the formula (I) and their salts or of intermediates generated in the course of the preparation.

The apparatuses listed lead to a modular procedure in which the individual passes are automated, but manual operations must be carried out between the passes. This can be circumvented by the use of partly or fully integrated automation systems, where the relevant automation modules are operated by, for example, robots. Such automation systems can be obtained for example from Caliper, Hopkinton, Mass. 01748, USA.

The performance of individual, or a plurality of, synthesis steps can be aided by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Besides the methods described herein, the preparation of compounds of the formula (I) and their salts can be effected fully or in part by solid-phase-supported methods. For this purpose, individual intermediates, or all intermediates, of the synthesis or of a synthesis adapted to the relevant procedure are bound to a synthesis resin. Solid-phase-supported synthesis methods are described sufficiently in the specialist literature, for example Barry A. Bunin in "The Combinatorial Index", Academic Press, 1998 and Combinatorial Chemistry—Synthesis, Analysis, Screening (Editor Günther Jung), Wiley, 1999. The use of solid-phase-supported synthesis methods permits a series of protocols known from the literature, which, again, can be carried out manually or in an automated manner. For example, the reactions can be carried out by means of IRORI technology in microreactors from Nexus Biosystems, 12140 Community Road, Poway, Calif. 92064, USA.

Carrying out individual or a plurality of synthesis steps, both on a solid and in the liquid phase, can be aided by the use of microwave technology. A series of experimental protocols are described in the specialist literature, for example in Microwaves in Organic and Medicinal Chemistry (Editors C. O. Kappe and A. Stadler), Wiley, 2005.

The preparation in accordance with the processes described herein generates compounds of the formula (I) and their salts in the form of substance collections, which are referred to as libraries. The present invention also relates to libraries which comprise at least two compounds of the formula (I) and their salts.

The compounds of the formula (I) according to the invention (and/or their salts), hereinbelow together referred to as "compounds according to the invention", have an outstanding herbicidal activity against a broad spectrum of economically important monocotyledonous and dicotyledonous annual harmful plants. The active substances also act efficiently on perennial harmful plants which produce shoots from rhizomes, woodstocks or other perennial organs and which are difficult to control.

The present invention therefore also relates to a method of controlling undesired plants or for regulating the growth of plants, preferably in crops of plants, where one or more compound(s) according to the invention is/are applied to the plants (for example harmful plants such as monocotyledonous or dicotyledonous weeds or undesired crop plants), to the seeds (for example grains, seeds or vegetative propagules such as tubers or shoot parts with buds) or to the area on which the plants grow (for example the area under cultivation). In this context, the compounds according to the invention can be applied for example pre-planting (if appropriate also by incorporation into the soil), pre-emergence or post-emergence. Examples of individual representatives of the monocotyledonous and dicotyledonous weed flora which can be controlled by the compounds according to the invention shall be mentioned, without the mention being intended as a limitation to certain species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum*.

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium*.

If the compounds according to the invention are applied to the soil surface before germination, either the emergence of the weed seedlings is prevented completely or the weeds grow until they have reached the cotyledon stage, but then stop their growth and, finally, die completely after three to four weeks have elapsed.

When the active substances are applied post-emergence to the green plant parts, growth stops after the treatment, and the harmful plants remain in the growth stage of the time of application or die fully after a certain period of time, so that competition by weeds, which is harmful to the crop plants, is thus eliminated at an early point in time and in a sustained manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, in particular *Zea* and *Triticum*, are damaged only to an insignificant extent, or not at all, depending on the structure of the respective compound according to the invention and its application rate. This is why the present compounds are highly suitable for the selective control of undesired plant growth in plant crops such as agriculturally useful plants or ornamentals.

Moreover, the compounds according to the invention (depending on their respective structure and the application rate applied) have outstanding growth-regulatory properties in crop plants. They engage in the plant metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting undesired vegetative growth without destroying the plants in the process. Inhibiting the vegetative growth plays an important role in many monocotyledonous and dicotyledonous crops since for example lodging can be reduced, or prevented completely, hereby.

Owing to their herbicidal and plant-growth-regulatory properties, the active substances can also be employed for controlling harmful plants and crops of genetically modified plants or plants which have been modified by conventional mutagenesis. As a rule, the transgenic plants are distinguished by especially advantageous properties, for example by resistances to certain pesticides, mainly certain herbicides, resistances to plant diseases or causative organisms of plant diseases, such as certain insects or microorganisms such as fungi, bacteria or viruses. Other special properties relate for example to the harvested material with regard to quantity, quality, storability, composition and specific constituents. Thus, transgenic plants with an increased starch content or a modified starch quality or those with a different fatty acid composition of the harvested material are known.

As regards transgenic crops, the use of the compounds according to the invention in economically important transgenic crops of useful plants and ornamentals, for example of cereals such as wheat, barley, rye, oats, sorghum and millet, rice and maize or else crops of sugar beet, cotton, soybean, oil seed rape, potato, tomato, peas and other vegetables is preferred. It is preferred to employ the compounds according to the invention as herbicides in crops of useful plants which are resistant, or have been made resistant by recombinant means, to the phytotoxic effects of the herbicides.

It is preferred to use the compounds according to the invention or their salts in economically important transgenic crops of useful plants and ornamentals, for example of cereals such as wheat, barley, rye, oats, sorghum and millet, rice, cassava and maize or else crops of sugar beet, cotton, soybean, oil seed rape, potato, tomato, peas and other vegetables. It is preferred to employ the compounds according to the invention as herbicides in crops of useful plants which are resistant, or have been made resistant by recombinant means, to the phytotoxic effects of the herbicides.

Conventional ways of generating novel plants which, in comparison with existing plants, have modified properties are, for example, traditional breeding methods and the generation of mutants. Alternatively, novel plants with modified properties can be generated with the aid of recombinant methods (see, for example, EP-A-0221044, EP-A-0131624). For example, the following have been described in several cases:
recombinant modifications of crop plants for the purposes of modifying the starch synthetized in the plants (for example WO 92/11376, WO 92/14827, WO 91/19806),
transgenic crop plants which are resistant to certain herbicides of the glufosinate type (cf., for example, EP-A-0242236, EP-A-242246) or of the glyphosate type (WO 92/00377) or of the sulfonylurea type (EP-A-0257993, U.S. Pat. No. 5,013,659),
transgenic crop plants, for example cotton, which is capable of producing Bacillus thuringiensis toxins (Bt toxins), which make the plants resistant to certain pests (EP-A-0142924, EP-A-0193259),
transgenic crop plants with a modified fatty acid composition (WO 91/13972), genetically modified crop plants with novel constituents or secondary metabolites, for example novel phytoalexins, which bring about an increased disease resistance (EPA 309862, EPA0464461),
genetically modified plants with reduced photorespiration which feature higher yields and higher stress tolerance (EPA 0305398),
transgenic crop plants which produce pharmaceutically or diagnostically important proteins ("molecular pharming"),
transgenic crop plants which are distinguished by higher yields or better quality,
transgenic crop plants which are distinguished by a combination, for example of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431).

To carry out such recombinant manipulations, it is possible to introduce nucleic acid molecules into plasmids, which permit a mutagenesis or sequence modification by recombination of DNA sequences. For example, base substitutions can be carried out, part-sequences can be removed, or natural or synthetic sequences may be added with the aid of standard methods. To link the DNA fragments with one another, it is possible to add adapters or linkers to the fragments; see, for example, Sambrook et al., 1989, Molecular Cloning, A Laboratory Manual, 2. ed., Cold Spring Harbor Laboratory Press, Cold Spring Harbor, N.Y.; or Winnacker "Gene and Klone", VCH Weinheim 2. ed., 1996

The generation of plant cells with a reduced activity for a gene product can be achieved for example by the expression of at least one corresponding antisense RNA, a sense RNA for achieving a cosuppression effect or by the expression of at least one correspondingly constructed ribozym, which specifically cleaves transcripts of the abovementioned gene product. To do this, it is possible firstly to use DNA molecules which comprise all of the coding sequence of a gene product, including any flanking sequences which may be present, or else DNA molecules which only comprise parts of the coding sequence, it being necessary for these parts to be long enough to bring about an antisense effect in the cells. It is also possible to use DNA sequences which have a high degree of homology with the coding sequences of a gene product, but which are not entirely identical.

When expressing nucleic acid molecules in plants, the protein synthetized may be localized in any compartment of the plant cell. In order to achieve localization in a particular compartment, however, it is possible for example to link the coding region to DNA sequences which ensure the localization in a specific compartment. Such sequences are known to the skilled worker (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). However, the nucleic acid molecules can also be expressed in the organelles of the plant cells.

The transgenic plant cells can be regenerated by known techniques to give intact plants. In principle, the transgenic plants may be plants of any plant species, that is to say both monocotyledonous and dicotyledonous plants.

Thus, transgenic plants can be obtained which feature modified properties as the result of overexpression, suppression or inhibition of homologous (=natural) genes or gene sequences or expression of heterologous (=foreign) genes or gene sequences.

It is preferred to employ the compounds according to the invention in transgenic crops which are resistant to growth regulators such as, for example, dicamba, or against herbicides which inhibit essential plant enzymes, for example acetolactate synthases (ALS), EPSP synthases, glutamine synthases (GS) or hydroxyphenylpyruvate dioxygenases (HPPD), or against herbicides from the group of the sulfonylureas, glyphosate, glufosinate or benzoylisoxazoles and analogous active substances.

When the active substances according to the invention are used in transgenic crops, effects are frequently observed—in addition to the effects on harmful plants which can be observed in other crops—which are specific for the application in the transgenic crop in question, for example a modified or specifically widened spectrum of weeds which can be controlled, modified application rates which may be employed for application, preferably good combiningability with the herbicides to which the transgenic crop is resistant, and an effect on growth and yield of the transgenic crop plants.

The invention therefore also relates to the use of the compounds according to the invention as herbicides for controlling harmful plants in transgenic crop plants.

The compounds according to the invention can be employed in the customary preparations in the form of wettable powders, emulsifiable concentrates, sprayable solutions, dusts or granules. The invention therefore also relates to herbicidal and plant-growth-regulating compositions which comprise the compounds according to the invention.

The compounds according to the invention can be formulated in various ways, depending on the prevailing biological and/or physico-chemical parameters. Examples of possible formulations are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing products, granules for application by broadcasting and on the soil, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical technology], volume 7, C. Hanser Verlag Munich, 4th Ed. 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are also known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active ethylene oxide adducts], Wiss. Verlagsgesell., Stuttgart 1976; Winnacker-Küchler, "Chemische Technologie" [Chemical technology], volume 7, C. Hanser Verlag Munich, 4th Ed. 1986.

Based on these formulations, it is also possible to prepare combinations with other pesticidally active substances such as, for example, insecticides, acaricides, herbicides, fungicides, and with safeners, fertilizers and/or growth regulators, for example in the form of a ready mix or a tank mix.

Wettable powders are preparations which are uniformly dispersible in water and which, besides the active substance, also comprise ionic and/or nonionic surfactants (wetters, dispersers), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, besides a diluent or inert substance. To prepare the wettable powders, the herbicidally active substances are ground finely, for example in customary apparatuses such as hammer mills, blower mills and air-jet mills, and mixed with the formulation auxiliaries, either simultaneously or subsequently.

Emulsifiable concentrates are prepared by dissolving the active substance in an organic solvent, for example butanol, cyclohexanone, dimethylformamide, xylene or else higher-boiling aromatics or hydrocarbons or mixtures of the organic solvents with addition of one or more ionic and/or nonionic surfactants (emulsifiers). Examples of emulsifiers which may be used are: calcium alkylarylsulfonates such as calcium dodecylbenzenesulfonate, or nonionic emulsifiers such as fatty acid polyglycol esters, alkylarylpolyglycol ethers, fatty alcohol polyglycol ethers, propylene oxide/ethylene oxide condensates, alkyl polyethers, sorbitan esters such as, for example, sorbitan fatty acid esters or polyoxyethylene sorbitan esters such as, for example, polyoxyethylene sorbitan fatty acid esters.

Dusts are obtained by grinding the active substance with finely divided solid materials such as, for example, talcum, natural clays such as kaolin, bentonite and pyrophyllite, or diatomaceous earth.

Suspension concentrates can be water- or oil-based. They can be prepared for example by wet-grinding by means of commercially available bead mills, if appropriate with addition of surfactants as already listed above for example in the case of the other formulation types.

Emulsions, for example oil-in-water emulsions (EW), can be prepared for example by means of stirrers, colloid mills and/or static mixers using aqueous organic solvents and, if appropriate, surfactants, as have already been mentioned for example above for the other formulation types.

Granules can be prepared either by spraying the active substance onto adsorptive, granulated inert material, or by applying active substance concentrates to the surface of carriers such as sand, kaolinites or granulated inert material with the aid of stickers, for example polyvinyl alcohol, sodium polyacrylate or else mineral oils. Suitable active substances can also be granulated in the manner which is customary for the production of fertilizer granules, if desired as a mixture with fertilizers.

Water-dispersible granules are generally prepared by customary methods such as spray drying, fluidized-bed granulation, disk granulation, mixing with high-speed stirrers, and extrusion without solid inert material.

To prepare disk granules, fluidized-bed granules, extruder granules and spray granules, see, for example, methods in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8-57.

For further details of the formulation of crop protection products see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

As a rule, the agrochemical preparations comprise from 0.1 to 99% by weight, in particular from 0.1 to 95% by weight, of compounds according to the invention. In wettable powders, the active substance concentration is, for example, approximately 10 to 90% by weight, the remainder to 100% by weight being composed of customary formulation constituents. In the case of emulsifiable concentrates, the active substance concentration can amount to approximately 1 to 90, preferably 5 to 80% by weight. Formulations in the form of dusts comprise from 1 to 30% by weight of active substance, preferably in most cases from 5 to 20% by weight of active substance, and sprayable solutions comprise approximately from 0.05 to 80, preferably from 2 to 50% by weight of active substance. In the case of water-dispersible granules, the active substance content depends partly on whether the active compound is in liquid or solid form, and on the granulation auxiliaries, fillers and the like which are being used. In the case of the water-dispersible granules, for example, the active substance content is between 1 and 95% by weight, preferably between 10 and 80% by weight.

In addition, the active substance formulations mentioned comprise, if appropriate, the auxiliaries which are conventional in each case, such as stickers, wetters, dispersants, emulsifiers, penetrations, preservatives, antifreeze agents, solvents, fillers, carriers, colorants, antifoams, evaporation inhibitors, and pH and viscosity regulators.

Based on these formulations, it is also possible to prepare combinations with other pesticidally active substances such as, for example, insecticides, acaricides, herbicides, fungicides, and with safeners, fertilizers and/or growth regulators, for example in the form of a ready mix or a tank mix.

Active substances which can be employed in combination with the compounds according to the invention in mixed formulations or in the tank mix are, for example, known active substances which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoen desaturase, photosystem I, photosystem II, protoporphyrinogen oxidase, as are described in, for example, Weed Research 26 (1986) 441-445 or "The Pesticide Manual", 14th edition, The British Crop Protection Council and the Royal Soc. of Chemistry, 2003 and the literature cited therein. Known herbicides or plant growth regulators which can be combined with the compounds according to the invention are, for example, the following active substances (the compounds are either designated by the common name according to the International Organization for Standardization (ISO) or by a chemical name, if appropriate together with the code number) and always comprise all use forms such as acids, salts, esters and isomers such as stereoisomers and optical isomers. In this context, one and in some cases also several use forms are mentioned by way of example:

acetochlor, acibenzolar, acibenzolar-S-methyl, acifluorfen, acifluorfen-sodium, aclonifen, alachlor, allidochlor, alloxydim, alloxydim-sodium, ametryne, amicarbazone, amidochlor, amidosulfuron, aminocyclopyrachlor, aminopyralid, amitrole, ammonium sulfamate, ancymidol, anilofos, asulam, atrazine, azafenidin, azimsulfuron, aziprotryne, BAH-043, BAS-140H, BAS-693H, BAS-714H, BAS-762H, BAS-776H, BAS-800H, beflubutamid, benazolin, benazolin-ethyl, bencarbazone, benfluralin, benfuresate, bensulide, bensulfuron-methyl, bentazone, benzfendizone, benzobicyclon, benzofenap, benzofluor, benzoylprop, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, chlorophthalim, chlorthal-dimethyl, chlorotoluron, chlorsulfuron, cinidon, cinidon-ethyl, cinmethylin, cinosulfuron, clethodim, clodinafop clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), di-allate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoro-propyl)-4,5-dihydro-5-oxo-1H-tetrazol-1-yl]-phenyl]ethanesulfonamide, fenoprop, fenoxaprop, fenoxaprop-P, fenoxaprop-ethyl, fenoxaprop-P-ethyl, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, flurochloridone, fluroxypyr, fluroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, L-glufosinate, L-glufosinate-ammonium, glufosinate-ammonium, glyphosate, glyphosate-isopropylammonium, H-9201, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HNPC-9908, HOK-201, HW-02, imazamethabenz, imazamethabenz-methyl, imazamox, imazapic, imazapyr, imazaquin, imazethapyr, imazosulfuron, inabenfide, indanofan, indoleacetic acid (IAA), 4-indol-3-ylbutyric acid (IBA), iodosulfuron, iodosulfuron-methyl-sodium, ioxynil, isocarbamid, isopropalin, isoproturon, isouron, isoxaben, isoxachlortole, isoxaflutole, isoxapyrifop, KUH-043, KUH-071, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulfuron, mesosulfuron-methyl, mesotrione, methabenzthiazuron, metam, metamifop, metamitron, metazachlor, methazole, methoxyphenone, methyldymron, 1-methylcyclopropene, methyl isothiocyanate, metobenzuron, metobenzuron, metobromuron, metolachlor, S-metolachlor, metosulam, metoxuron, metribuzin, metsulfuron, metsulfuron-methyl, molinate, monalide, monocarbamide, monocarbamide dihydrogen sulfate, monolinuron, monosulfuron, monuron, MT 128, MT-5950, i.e. N-[3-chloro-4-(1-methylethyl)-phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolat-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazol, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron-ethyl, pyrazoxyfen, pyribambenz, pyribambenz-isopropyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, sulcotrione, sulf-allate (CDEC), sulfentrazone, sulfometuron, sulfometuron-methyl, sulfosate (glyphosate-trimesium), sulfosulfuron, SYN-523, SYP-249, SYP-298, SYP-300, tebutam, tebuthiuron, tecnazene, tefuryltrione, tembotrione, tepraloxydim, terbacil, terbucarb, terbuchlor, terbumeton, terbuthylazine, terbutryne, TH-547, thenylchlor, thiafluamide, thiazafluron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, tri-allate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0166, ZJ-0270, ZJ-0543, ZJ-0862 and the following compounds

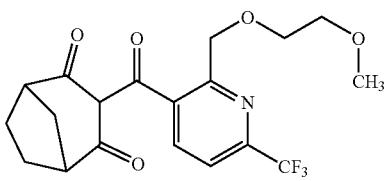

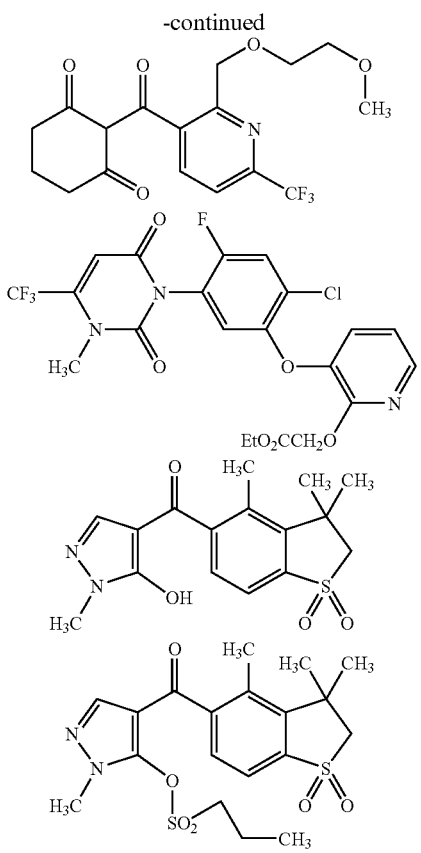

For use, the formulations, which are present in commercially available form, if appropriate, are diluted in the customary manner, for example using water in the case of wettable powders, emulsifiable concentrates, dispersions and water-dispersible granules. Preparations in the form of dusts, soil granules, granules for broadcasting, and sprayable solutions, are usually not diluted further with further inert substances prior to use.

The application rate required of the compounds of the formula (I) varies as a function of the external conditions such as temperature, humidity, the nature of the herbicide used and the like. It can vary within wide limits, for example between 0.001 and 1.0 kg/ha and more of active substance, but it is preferably between 0.005 and 750 g/ha.

The examples which follow are intended to illustrate the invention.

A. CHEMICAL EXAMPLES

1. Preparation of 5-cyclopropyl-4-(3-methylamino-2-methylsulfonyl-4-trifluoromethylbenzoyl)isoxazole (No. 184 of table A)

Step 1: Synthesis of 3-fluoro-2-methylthio-4-trifluoromethylbenzoic Acid 25.0 g (120.1 mmol) of 3-fluoro-4-trifluoromethylbenzoic acid were dissolved in 250 ml of dry tetrahydrofuran (THF), and 100.9 ml of n-butyllithium (2.5 M in hexane, 252.3 mmol) were added dropwise at −40° C. The mixture was stirred for 3 h, and a solution of 32.5 ml (360.4 mmol) of dimethyl disulfide in 50 ml of dry THF was then added dropwise. The mixture was stirred for 16 h, during which process, after half an hour, the temperature climbed slowly to RT. For work-up, 2 M HCl was added carefully. The mixture was extracted with diethyl ether, and the organic phase was subsequently extracted with 2 M NaOH. The aqueous phase was acidified and extracted with diethyl ether. The organic phase was washed with water, dried, and the solvent was removed in vacuo. The residue was stirred with n-heptane and the solid was separated off by a filtration. This gave 17.0 g of crude product, which was employed in the next synthesis step without further purification.

Step 2: Synthesis of 3-fluoro-2-methylsulfonyl-4-trifluoromethylbenzoic Acid 18.6 g (73.2 mmol) of 3-fluoro-2-methylthio-4-trifluoromethylbenzoic acid were introduced into 180 ml of glacial acetic acid. 724 mg (2.2 mmol) of sodium tungstate(VI) dihydrate were added, and the mixture was then heated to 50-60° C. 15.0 ml (30% strength, 146.8 mmol) of an aqueous hydrogen peroxide solution were added dropwise at this temperature. The mixture was stirred for 4.5 h at this temperature. To complete the reaction, 14.9 ml (30% strength, 145.9 mmol) of an aqueous $H_2O_2$ solution were subsequently carefully added dropwise, and the contents stirred for another 3 h at 50-60° C. The reaction mixture was cooled and, for work-up, poured into water. The mixture was extracted twice using ethyl acetate, the combined organic phases were washed with an aqueous saturated sodium hydrogen sulfite solution, and, after the absence of peroxides has been determined analytically, the mixture was dried and the solvent was removed in vacuo. This gave 19.8 g of product in 95% purity.

Step 3: Synthesis of 3-methylamino-2-methylsulfonyl-4-trifluoromethylbenzoic Acid 2.40 g (8.4 mmol) of 3-fluoro-2-methylsulfonyl-4-trifluoromethylbenzoic acid were treated with 12.1 ml (168 mmol; 40 percent strength) of aqueous methylamine solution and the mixture was stirred for 4 h at RT. For work-up, the contents were poured into 6 N HCl, the mixture was subsequently cooled in an ice-bath. The precipitate was filtered off with suction. This gave 2.50 g of product in 95% purity.

Step 4: Synthesis of tert-butyl 3-cyclopropyl-2-(3-methylamino-2-methylsulfonyl-4-trifluoroethylbenzoyl)-3-oxopropanoate 2.50 g (8.4 mmol) of 3-methylamino-2-methylsulfonyl-4-trifluoromethylbenzoic acid were introduced into 50 ml of $CH_2Cl_2$ and treated with 1.1 ml (12.6 mmol) oxalyl dichloride and two drops of DMF. The mixture was heated at reflux until the evolution of gas had ceased. To complete the reaction, another 0.8 ml (9.2 mmol) of oxalyl dichloride and two more drops of DMF were added. After the evolution of gas had ceased, the contents were heated at reflux for another 15 min. Thereafter, the mixture was concentrated on a rotary evaporator. To remove a residual oxalyl dichloride, the residue was coevaporated with toluene. The residue was taken up in 50 ml of toluene. 4.01 g (16.8 mmol) of magnesium (3-tert.-butoxy-1-cyclopropyl-3-oxoprop-1-en-1-olate)methoxide (synthesis described for example in EP 0918056) were added, and the mixture was stirred for 16 h at RT. The contents were concentrated and the residue was taken up in ethyl acetate. The solution was washed with dilute HCl, the organic phase was dried, and the solvent was removed in vacuo. This gave 5.3 g of crude product in approximately 70% purity, which was employed in the next synthesis step without further purification.

Step 5: Synthesis of 1-cyclopropyl-3-(3-methylamino-2-methylsulfonyl-4-trifluoromethylphenyl)propane-1,3-dione 5.0 ml of trifluoroacetic acid were heated at 55°-60° C. A solution of 5.3 g (8.0 mmol; 70% purity) of tert-butyl-3-cyclopropyl-2-(3-methylamino-2-methylsulfonyl-4-trifluoromethylbenzoyl)-3-oxopropanoate in 10 ml of $CH_2Cl_2$ was added dropwise and the mixture was then heated at reflux for 15 min. The solvent was removed in vacuo and the residue was purified by column chromatography on silica gel. This gave 1.22 g of product in 95% purity.

Step 6: Synthesis of 1-cyclopropyl-2-(dimethylaminomethylidene)-3-(3-methylamino-2-methylsulfonyl-4-trifluoromethylphenyl)propane-1,3-dione 1.22 g (3.4 mmol) of 1-cyclopropyl-3-(3-methylamino-2-methylsulfonyl-4-trifluoromethylphenyl)propane-1,3-dione were treated with 3.0 ml (22.7 mmol) of N,N-dimethyl formamide dimethyl acetal and the mixture was stirred for 16 h at RT. Then, a little n-heptane was added, and the contents were stirred for a further 10 min at RT. The precipitate was filtered off with suction. This gave 1.29 g of product in 95% purity.

Step 7: Synthesis of 5-cyclopropyl-4-(3-methylamino-2-methylsulfonyl-4-trifluoromethylbenzoyl)isoxazole 1.29 g (3.1 mmol) of 1-cyclopropyl-2-(dimethylaminomethylidene)-3-(3-methylamino-2-methylsulfonyl-4-trifluoromethylphenyl)propane-1,3-dione were introduced into 50 ml of ethanol. 0.30 g (4.3 mmol) of hydroxylammonium chloride was added, and the mixture was stirred for 30 min at RT. Thereafter, 0.33 g (4.0 mmol) of sodium acetate was added, and the contents were stirred for 16 h at RT. Thereupon, a further 0.15 g (2.2 mmol) of hydroxylammonium chloride was added, and, again, the mixture was stirred for 16 h at RT. Thereafter, a further 0.15 g (2.2 mmol) of hydroxylammonium chloride was added, and the mixture was stirred for a further 3 d at RT. The solvent was removed in vacuo, and the residue was taken up in ethyl acetate. The solution was washed with 1 N HCl, the organic phase was dried, and the solvent was removed in vacuo. The residue was purified by column chromatography on silica gel. This gave 1.00 g of product in 95% purity.

2. Preparation of 5-cyclopropyl-4-(3-methylamino-2-methyl-4-methylsulfonyl-benzoyl)isoxazole (No. 2 of Table A)

Step 1: Synthesis of 1-cyclopropyl-2-(dimethylaminomethylidene)-3-(3-methylamino-2-methyl-4-methylsulfonylphenyl)propane-1,3-dione A solution of 1.58 g (5.1 mmol) of 1-cyclopropyl-3-(3-methylamino-2-methyl-4-methylsulfonylphenyl)propane-1,3-dione and 2.0 ml (15.3 mmol) of N,N-dimethyl formamide dimethyl acetal was stirred for 3 h at RT. The mixture was treated with 10 ml of $CH_2Cl_2$, stirred for 2 h at an oil-bath temperature of 50° C., left to stand overnight, stirred for 1 d at an oil-bath temperature of 50° C., and the solvent was removed in vacuo. The residue was purified by column chromatography on silica gel. This gave 0.85 g of product in 93% purity.

Step 2: Synthesis of 5-cyclopropyl-4-(3-methylamino-2-methyl-4-methylsulfonyl-benzoyl)isoxazole 0.19 g (2.8 mmol) of hydroxylammonium chloride was added to a solution of 0.85 g (2.3 mmol) of 1-cyclopropyl-2-(dimethylaminomethylidene)-3-(3-methylamino-2-methyl-4-methylsulfonylphenyl)propane-1,3-dione in 100 ml of ethanol. The mixture was stirred for 3 h at RT, and the solvent was removed in vacuo. The residue was taken up in $CH_2Cl_2$, washed with 10% strength $H_2SO_4$ and dried over $MgSO_4$. The solvent was removed in vacuo, and the residue was purified by column chromatography on silica gel. This gave 0.50 g of product in 95% purity.

The examples listed in the tables hereinbelow were prepared analogously to abovementioned methods or are obtainable analogously to abovementioned methods. These compounds are very particularly preferred.

The abbreviations used are:

All=allyl Et=ethyl Me=methyl Pr=propyl

TABLE A

Compounds of the formula (I) according to the invention (I)

| No. | X | Y | A | Z | Physical data: $^1$H NMR: δ [CDCl$_3$] |
|---|---|---|---|---|---|
| 1 | Me | SO$_2$Me | NH$_2$ | H | 8.18 (s, 1H), 7.76 (d, 1H), 6.80 (d, 1H), 5.32 (br, 2H), 3.11 (s, 3H), 2.62-2.71 (m, 1H), 2.18 (s, 3H), 1.34-1.40 (m, 2H), 1.22-1.29 (m, 2H) |
| 2 | Me | SO$_2$Me | NHMe | H | 8.21 (s, 1H), 7.82 (d,1H), 6.96 (d, 1H), 5.62 (br, 1H), 3.09 (s, 3H), 3.01 (s, 3H), 2.56-2.64 (m, 1H), 2.32 (s, 3H), 1.33-1.40 (m, 2H), 1.21-1.27 (m, 2H) |
| 3 | Me | SO$_2$Me | NHEt | H | 8.21 (s, 1H), 7.82 (d, 1H), 6.97 (d, 1H), 5.55 (br, 1H), 3.27 (q, 2H), 3.11 (s, 3H), 2.57-2.65 (m, 1H), 2.29 (s, 3H), 1.33-1.39 (m, 2H), 1.31 (t, 3H), 1.22-1.28 (m, 2H) |
| 4 | Me | SO$_2$Me | NH-n-Pr | H | 8.21 (s, 1H), 7.82 (d, 1H), 6.95 (d, 1H), 5.68 (br, 1H), 3.18 (dd, 2H), 3.11 (s, 3H), 2.56-2.63 (m, 1H), 2.29 (s, 3H), 1.66-1.76 (m, 2H), 1.34-1.39 (m, 2H), 1.21-1.28 (m, 2H), 1.03 (t, 3H) |
| 5 | Me | SO$_2$Me | NHAll | H | 8.19 (s, 1H), 7.84 (d, 1H), 6.98 (d, 1H), 5.93.6.05 (m, 1H), 5.68 (br, 1H), 5.32-5.39 (m, 1H), 5.2-5.25 (m, 1H), 3.82-3.88 (m, 2H), 3.11 (s, 3H), 2.58-2.66 (m, 1H), 2.29 (s, 3H), 1.33-1.39 (m, 2H), 1.21-1.28 (m, 2H) |
| 6 | Me | SO$_2$Me | NH(CH$_2$)$_2$O—Me | H | 8.21 (s, 1H), 7.84 (d, 1H), 6.97 (d, 1H), 5.81 (br, 1H), 3.62 (dd, 2H), 3.42 (br, 2H), 3.41 (s, 3H), 3.21 (s, 3H), 2.54-2.62 (m, 1H), 2.29 (s, 3H), 1.33-1.39 (m, 2H), 1.21-1.28 (m, 2H) |
| 7 | Me | SO$_2$Me | NH(CH$_2$)$_2$O—Et | H | 8.22 (s, 1H), 7.84 (d, 1H), 6.97 (d, 1H), 5.84 (br, 1H), 3.66 (dd, 2H), 3.57 (q, 2H), 3.42 (dd, 2H), 3.21 (s, 3H), 2.53-2.63 (m, 1H), 2.29 (s, 3H), 1.32-1.40 (m, 2H), 1.24 (t, 3H), 1.19-1.29 (m, 2H) |
| 8 | Me | SO$_2$Me | NH(CH$_2$)$_3$O—Me | H | 8.21 (s, 1H), 7.83 (d,1H), 6.98 (d, 1H), 5.64 (br, 1H), 3.55 (t, 2H), 3.37 (s, 3H), 3.32 (t, 2H), 3.13 (s, 3H), 2.55-2.63 (m, 1H), 2.30 (s, 3H), 1.90-1.99 (m, 2H), 1.34-1.39 (m, 2H), 1.21-1.28 (m, 2H) |
| 9 | Me | SO$_2$Me | N=CH—NMe$_2$ | H | |
| 10 | Me | SO$_2$Me | NH$_2$ | CO$_2$Me | |
| 11 | Me | SO$_2$Me | NHMe | CO$_2$Me | |
| 12 | Me | SO$_2$Me | NHEt | CO$_2$Me | |
| 13 | Me | SO$_2$Me | NH-n-Pr | CO$_2$Me | |
| 14 | Me | SO$_2$Me | NHAll | CO$_2$Me | |
| 15 | Me | SO$_2$Me | NH(CH$_2$)$_2$O—Me | CO$_2$Me | |
| 16 | Me | SO$_2$Me | N=CH—NMe$_2$ | CO$_2$Me | |
| 17 | Me | SO$_2$Me | N=CH—NMe$_2$ | CO$_2$Et | |
| 18 | Me | SO$_2$Me | NH$_2$ | CO$_2$Et | |

TABLE A-continued

Compounds of the formula (I) according to the invention

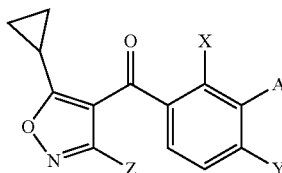

(I)

| No. | X | Y | A | Z | Physical data: $^1$H NMR: δ [CDCl$_3$] |
|---|---|---|---|---|---|
| 19 | Me | SO$_2$Me | NHMe | CO$_2$Et | |
| 20 | Me | SO$_2$Me | NHEt | CO$_2$Et | |
| 21 | Me | SO$_2$Me | NH-n-Pr | CO$_2$Et | |
| 22 | Me | SO$_2$Me | NHAll | CO$_2$Et | |
| 23 | Me | SO$_2$Me | NH(CH$_2$)$_2$O—Me | CO$_2$Et | |
| 24 | Me | SO$_2$Me | NMe$_2$ | H | 8.18 (s, 1H), 8.04 (d, 1H), 7.32 (d, 1H), 3.29 (s, 3H), 2.93 (s, 6H), 2.58-2.66 (m, 1H), 2.37 (s, 3H), 1.34-1.40 (m, 2H), 1.22-1.29 (m, 2H) |
| 25 | Me | SO$_2$Me | N(Me)Et | H | |
| 26 | Me | SO$_2$Me | N(Me)-n-Pr | H | |
| 27 | Me | SO$_2$Me | N(Me)All | H | |
| 28 | Me | SO$_2$Me | N(Me)(CH$_2$)$_2$O—Me | H | |
| 29 | Me | SO$_2$Me | NMe$_2$ | CO$_2$Me | |
| 30 | Me | SO$_2$Me | N(Me)Et | CO$_2$Me | |
| 31 | Me | SO$_2$Me | N(Me)-n-Pr | CO$_2$Me | |
| 32 | Me | SO$_2$Me | N(Me)All | CO$_2$Me | |
| 33 | Me | SO$_2$Me | N(Me)(CH$_2$)$_2$O—Me | CO$_2$Me | |
| 34 | Me | SO$_2$Me | NMe$_2$ | CO$_2$Et | |
| 35 | Me | SO$_2$Me | N(Me)Et | CO$_2$Et | |
| 36 | Me | SO$_2$Me | N(Me)-n-Pr | CO$_2$Et | |
| 37 | Me | SO$_2$Me | N(Me)All | CO$_2$Et | |
| 38 | Me | SO$_2$Me | N(Me)(CH$_2$)$_2$O—Me | CO$_2$Et | |
| 39 | Me | CF$_3$ | NH$_2$ | H | |
| 40 | Me | CF$_3$ | NHMe | H | |
| 41 | Me | CF$_3$ | NHEt | H | |
| 42 | Me | CF$_3$ | NH-n-Pr | H | |
| 43 | Me | CF$_3$ | NHAll | H | |
| 44 | Me | CF$_3$ | NH(CH$_2$)$_2$O—Me | H | |
| 45 | Me | CF$_3$ | N=CH—NMe$_2$ | H | |
| 46 | Me | CF$_3$ | NH$_2$ | CO$_2$Me | |
| 47 | Me | CF$_3$ | NHMe | CO$_2$Me | |
| 48 | Me | CF$_3$ | NHEt | CO$_2$Me | |
| 49 | Me | CF$_3$ | NH-n-Pr | CO$_2$Me | |
| 50 | Me | CF$_3$ | NHAll | CO$_2$Me | |
| 51 | Me | CF$_3$ | NH(CH$_2$)$_2$O—Me | CO$_2$Me | |
| 52 | Me | CF$_3$ | N=CH—NMe$_2$ | CO$_2$Me | |
| 53 | Me | CF$_3$ | NH$_2$ | CO$_2$Et | |
| 54 | Me | CF$_3$ | NHMe | CO$_2$Et | |
| 55 | Me | CF$_3$ | NHEt | CO$_2$Et | |
| 56 | Me | CF$_3$ | NH-n-Pr | CO$_2$Et | |
| 57 | Me | CF$_3$ | NHAll | CO$_2$Et | |
| 58 | Me | CF$_3$ | NH(CH$_2$)$_2$O—Me | CO$_2$Et | |
| 59 | Me | CF$_3$ | N=CH—NMe$_2$ | CO$_2$Et | |
| 60 | Me | CF$_3$ | NMe$_2$ | H | |
| 61 | Me | CF$_3$ | N(Me)Et | H | |
| 62 | Me | CF$_3$ | N(Me)-n-Pr | H | |
| 63 | Me | CF$_3$ | N(Me)All | H | |
| 64 | Me | CF$_3$ | N(Me)(CH$_2$)$_2$O—Me | H | |
| 65 | Me | CF$_3$ | NMe$_2$ | CO$_2$Me | |
| 66 | Me | CF$_3$ | N(Me)Et | CO$_2$Me | |
| 67 | Me | CF$_3$ | N(Me)-n-Pr | CO$_2$Me | |
| 68 | Me | CF$_3$ | N(Me)All | CO$_2$Me | |
| 69 | Me | CF$_3$ | N(Me)(CH$_2$)$_2$O—Me | CO$_2$Me | |
| 70 | Me | CF$_3$ | NMe$_2$ | CO$_2$Et | |
| 71 | Me | CF$_3$ | N(Me)Et | CO$_2$Et | |
| 72 | Me | CF$_3$ | N(Me)-n-Pr | CO$_2$Et | |
| 73 | Me | CF$_3$ | N(Me)All | CO$_2$Et | |
| 74 | Me | CF$_3$ | N(Me)(CH$_2$)$_2$O—Me | CO$_2$Et | |
| 75 | Me | Cl | NH$_2$ | H | |
| 76 | Me | Cl | NHMe | H | |
| 77 | Me | Cl | NHEt | H | |
| 78 | Me | Cl | NH-n-Pr | H | |
| 79 | Me | Cl | NHAll | H | |

TABLE A-continued

Compounds of the formula (I) according to the invention (I)

| No. | X | Y | A | Z | Physical data: $^1$H NMR: δ [CDCl$_3$] |
|---|---|---|---|---|---|
| 80 | Me | Cl | NH(CH$_2$)$_2$O—Me | H | |
| 81 | Me | Cl | N=CH—NMe$_2$ | H | |
| 82 | Me | Cl | NH$_2$ | CO$_2$Me | |
| 83 | Me | Cl | NHMe | CO$_2$Me | |
| 84 | Me | Cl | NHEt | CO$_2$Me | |
| 85 | Me | Cl | NH-n-Pr | CO$_2$Me | |
| 86 | Me | Cl | NHAll | CO$_2$Me | |
| 87 | Me | Cl | NH(CH$_2$)$_2$O—Me | CO$_2$Me | |
| 88 | Me | Cl | N=CH—NMe$_2$ | CO$_2$Me | |
| 89 | Me | Cl | NH$_2$ | CO$_2$Et | |
| 90 | Me | Cl | NHMe | CO$_2$Et | |
| 91 | Me | Cl | NHEt | CO$_2$Et | |
| 92 | Me | Cl | NH-n-Pr | CO$_2$Et | |
| 93 | Me | Cl | NHAll | CO$_2$Et | |
| 94 | Me | Cl | NH(CH$_2$)$_2$O—Me | CO$_2$Et | |
| 95 | Me | Cl | N=CH—NMe$_2$ | CO$_2$Et | |
| 96 | Me | Cl | NMe$_2$ | H | |
| 97 | Me | Cl | N(Me)Et | H | |
| 98 | Me | Cl | N(Me)-n-Pr | H | |
| 99 | Me | Cl | N(Me)All | H | |
| 100 | Me | Cl | N(Me)(CH$_2$)$_2$O—Me | H | |
| 101 | Me | Cl | NMe$_2$ | CO$_2$Me | |
| 102 | Me | Cl | N(Me)Et | CO$_2$Me | |
| 103 | Me | Cl | N(Me)-n-Pr | CO$_2$Me | |
| 104 | Me | Cl | N(Me)All | CO$_2$Me | |
| 105 | Me | Cl | N(Me)(CH$_2$)$_2$O—Me | CO$_2$Me | |
| 106 | Me | Cl | NMe$_2$ | CO$_2$Et | |
| 107 | Me | Cl | N(Me)Et | CO$_2$Et | |
| 108 | Me | Cl | N(Me)-n-Pr | CO$_2$Et | |
| 109 | Me | Cl | N(Me)All | CO$_2$Et | |
| 110 | Me | Cl | N(Me)(CH$_2$)$_2$O—Me | CO$_2$Et | |
| 111 | Me | OMe | NH$_2$ | H | |
| 112 | Me | OMe | NHMe | H | |
| 113 | Me | OMe | NHEt | H | |
| 114 | Me | OMe | NH-n-Pr | H | |
| 115 | Me | OMe | NHAll | H | |
| 116 | Me | OMe | NH(CH$_2$)$_2$O—Me | H | |
| 117 | Me | OMe | N=CH—NMe$_2$ | H | |
| 118 | Me | OMe | NH$_2$ | CO$_2$Me | |
| 119 | Me | OMe | NHMe | CO$_2$Me | |
| 120 | Me | OMe | NHEt | CO$_2$Me | |
| 121 | Me | OMe | NH-n-Pr | CO$_2$Me | |
| 122 | Me | OMe | NHAll | CO$_2$Me | |
| 123 | Me | OMe | NH(CH$_2$)$_2$O—Me | CO$_2$Me | |
| 124 | Me | OMe | N=CH—NMe$_2$ | CO$_2$Me | |
| 125 | Me | OMe | NH$_2$ | CO$_2$Et | |
| 126 | Me | OMe | NHMe | CO$_2$Et | |
| 127 | Me | OMe | NHEt | CO$_2$Et | |
| 128 | Me | OMe | NH-n-Pr | CO$_2$Et | |
| 129 | Me | OMe | NHAll | CO$_2$Et | |
| 130 | Me | OMe | NH(CH$_2$)$_2$O—Me | CO$_2$Et | |
| 131 | Me | OMe | N=CH—NMe$_2$ | CO$_2$Et | |
| 132 | Me | OMe | NMe$_2$ | H | |
| 133 | Me | OMe | N(Me)Et | H | |
| 134 | Me | OMe | N(Me)-n-Pr | H | |
| 135 | Me | OMe | N(Me)All | H | |
| 136 | Me | OMe | N(Me)(CH$_2$)$_2$O—Me | H | |
| 137 | Me | OMe | NMe$_2$ | CO$_2$Me | |
| 138 | Me | OMe | N(Me)Et | CO$_2$Me | |
| 139 | Me | OMe | N(Me)-n-Pr | CO$_2$Me | |
| 140 | Me | OMe | N(Me)All | CO$_2$Me | |
| 141 | Me | OMe | N(Me)(CH$_2$)$_2$O—Me | CO$_2$Me | |
| 142 | Me | OMe | NMe$_2$ | CO$_2$Et | |
| 143 | Me | OMe | N(Me)Et | CO$_2$Et | |

TABLE A-continued

Compounds of the formula (I) according to the invention $$\text{(I)}$$

| No. | X | Y | A | Z | Physical data: $^1$H NMR: δ [CDCl$_3$] |
|---|---|---|---|---|---|
| 144 | Me | OMe | N(Me)-n-Pr | CO$_2$Et | |
| 145 | Me | OMe | N(Me)All | CO$_2$Et | |
| 146 | Me | OMe | N(Me)(CH$_2$)$_2$O—Me | CO$_2$Et | |
| 147 | SO$_2$Me | SO$_2$Me | NH$_2$ | H | |
| 148 | SO$_2$Me | SO$_2$Me | NHMe | H | |
| 149 | SO$_2$Me | SO$_2$Me | NHEt | H | |
| 150 | SO$_2$Me | SO$_2$Me | NH-n-Pr | H | |
| 151 | SO$_2$Me | SO$_2$Me | NHAll | H | |
| 152 | SO$_2$Me | SO$_2$Me | NH(CH$_2$)$_2$O—Me | H | |
| 153 | SO$_2$Me | SO$_2$Me | N=CH—NMe$_2$ | H | |
| 154 | SO$_2$Me | SO$_2$Me | NH$_2$ | CO$_2$Me | |
| 155 | SO$_2$Me | SO$_2$Me | NHMe | CO$_2$Me | |
| 156 | SO$_2$Me | SO$_2$Me | NHEt | CO$_2$Me | |
| 157 | SO$_2$Me | SO$_2$Me | NH-n-Pr | CO$_2$Me | |
| 158 | SO$_2$Me | SO$_2$Me | NHAll | CO$_2$Me | |
| 159 | SO$_2$Me | SO$_2$Me | NH(CH$_2$)$_2$O—Me | CO$_2$Me | |
| 160 | SO$_2$Me | SO$_2$Me | N=CH—NMe$_2$ | CO$_2$Me | |
| 161 | SO$_2$Me | SO$_2$Me | NH$_2$ | CO$_2$Et | |
| 162 | SO$_2$Me | SO$_2$Me | NHMe | CO$_2$Et | |
| 163 | SO$_2$Me | SO$_2$Me | NHEt | CO$_2$Et | |
| 164 | SO$_2$Me | SO$_2$Me | NH-n-Pr | CO$_2$Et | |
| 165 | SO$_2$Me | SO$_2$Me | NHAll | CO$_2$Et | |
| 166 | SO$_2$Me | SO$_2$Me | NH(CH$_2$)$_2$O—Me | CO$_2$Et | |
| 167 | SO$_2$Me | SO$_2$Me | N=CH—NMe$_2$ | CO$_2$Et | |
| 168 | SO$_2$Me | SO$_2$Me | NMe$_2$ | H | |
| 169 | SO$_2$Me | SO$_2$Me | N(Me)Et | H | |
| 170 | SO$_2$Me | SO$_2$Me | N(Me)-n-Pr | H | |
| 171 | SO$_2$Me | SO$_2$Me | N(Me)All | H | |
| 172 | SO$_2$Me | SO$_2$Me | N(Me)(CH$_2$)$_2$O—Me | H | |
| 173 | SO$_2$Me | SO$_2$Me | NMe$_2$ | CO$_2$Me | |
| 174 | SO$_2$Me | SO$_2$Me | N(Me)Et | CO$_2$Me | |
| 175 | SO$_2$Me | SO$_2$Me | N(Me)-n-Pr | CO$_2$Me | |
| 176 | SO$_2$Me | SO$_2$Me | N(Me)All | CO$_2$Me | |
| 177 | SO$_2$Me | SO$_2$Me | N(Me)(CH$_2$)$_2$O—Me | CO$_2$Me | |
| 178 | SO$_2$Me | SO$_2$Me | NMe$_2$ | CO$_2$Et | |
| 179 | SO$_2$Me | SO$_2$Me | N(Me)Et | CO$_2$Et | |
| 180 | SO$_2$Me | SO$_2$Me | N(Me)-n-Pr | CO$_2$Et | |
| 181 | SO$_2$Me | SO$_2$Me | N(Me)All | CO$_2$Et | |
| 182 | SO$_2$Me | SO$_2$Me | N(Me)(CH$_2$)$_2$O—Me | CO$_2$Et | |
| 183 | SO$_2$Me | CF$_3$ | NH$_2$ | H | 8.21 (s, 1H), 7.72 (d,1H), 6.67 (d, 1H), 6.12 (br. s, 2H), 3.25 (s, 3H), 2.57 (m, 1H), 1.38-1.32 (m, 2H), 1.25-1.22 (m, 2H) |
| 184 | SO$_2$Me | CF$_3$ | NHMe | H | 8.19 (s, 1H), 7.83 (d, 1H), 6.97 (q, 1H), 6.68 (d, 1H), 3.23 (s, 3H), 3.12 (m, 3H), 2.57 (m, 1H), 1.37-1.32 (m, 2H), 1.26-1.20 (m, 2H) |
| 185 | SO$_2$Me | CF$_3$ | NHEt | H | 8.21 (s, 1H), 7.83 (d,1H), 6.71 (d,1H), 6.63 (t, 1H), 3.42 (m, 2H), 3.27 (s, 3H), 2.58 (m, 1H), 1.38-1.32 (m, 2H), 1.25-1.20 (m, 2H) |
| 186 | SO$_2$Me | CF$_3$ | NH-n-Pr | H | |
| 187 | SO$_2$Me | CF$_3$ | NHAll | H | |
| 188 | SO$_2$Me | CF$_3$ | NH(CH$_2$)$_2$O—Me | H | |
| 189 | SO$_2$Me | CF$_3$ | N=CH—NMe$_2$ | H | |
| 190 | SO$_2$Me | CF$_3$ | NH$_2$ | CO$_2$Me | |
| 191 | SO$_2$Me | CF$_3$ | NHMe | CO$_2$Me | |
| 192 | SO$_2$Me | CF$_3$ | NHEt | CO$_2$Me | |
| 193 | SO$_2$Me | CF$_3$ | NH-n-Pr | CO$_2$Me | |
| 194 | SO$_2$Me | CF$_3$ | NHAll | CO$_2$Me | |
| 195 | SO$_2$Me | CF$_3$ | NH(CH$_2$)$_2$O—Me | CO$_2$Me | |
| 196 | SO$_2$Me | CF$_3$ | N=CH—NMe$_2$ | CO$_2$Me | |
| 197 | SO$_2$Me | CF$_3$ | NH$_2$ | CO$_2$Et | 7.68 (d, 1H), 6.66 (d, 1H), 6.08 (br. s, 2H), 4.18 (q, 2H), 3.27 (s, 3H), 2.48 (m, |

TABLE A-continued

Compounds of the formula (I) according to the invention (I)

| No. | X | Y | A | Z | Physical data: $^1$H NMR: δ [CDCl$_3$] |
|---|---|---|---|---|---|
| | | | | | 1H), 1.37-1.32 (m, 2H), 1.28-1.20 (t + m, 5H) |
| 198 | SO$_2$Me | CF$_3$ | NHMe | CO$_2$Et | |
| 199 | SO$_2$Me | CF$_3$ | NHEt | CO$_2$Et | |
| 200 | SO$_2$Me | CF$_3$ | NH-n-Pr | CO$_2$Et | |
| 201 | SO$_2$Me | CF$_3$ | NHAll | CO$_2$Et | |
| 202 | SO$_2$Me | CF$_3$ | NH(CH$_2$)$_2$O—Me | CO$_2$Et | |
| 203 | SO$_2$Me | CF$_3$ | N=CH—NMe$_2$ | CO$_2$Et | |
| 204 | SO$_2$Me | CF$_3$ | NMe$_2$ | H | 8.12 (s, 1H), 7.98 (d, 1H), 7.32 (d, 1H), 3.32 (s, 3H), 2.92 (s, 6H), 2.67 (m, 1H), 1.38-1.33 (m, 2H), 1.27-1.22 (m, 2H) |
| 205 | SO$_2$Me | CF$_3$ | N(Me)Et | H | |
| 206 | SO$_2$Me | CF$_3$ | N(Me)-n-Pr | H | |
| 207 | SO$_2$Me | CF$_3$ | N(Me)All | H | |
| 208 | SO$_2$Me | CF$_3$ | N(Me)(CH$_2$)$_2$O—Me | H | |
| 209 | SO$_2$Me | CF$_3$ | NMe$_2$ | CO$_2$Me | |
| 210 | SO$_2$Me | CF$_3$ | N(Me)Et | CO$_2$Me | |
| 211 | SO$_2$Me | CF$_3$ | N(Me)-n-Pr | CO$_2$Me | |
| 212 | SO$_2$Me | CF$_3$ | N(Me)All | CO$_2$Me | |
| 213 | SO$_2$Me | CF$_3$ | N(Me)(CH$_2$)$_2$O—Me | CO$_2$Me | |
| 214 | SO$_2$Me | CF$_3$ | NMe$_2$ | CO$_2$Et | |
| 215 | SO$_2$Me | CF$_3$ | N(Me)Et | CO$_2$Et | |
| 216 | SO$_2$Me | CF$_3$ | N(Me)-n-Pr | CO$_2$Et | |
| 217 | SO$_2$Me | CF$_3$ | N(Me)All | CO$_2$Et | |
| 218 | SO$_2$Me | CF$_3$ | N(Me)(CH$_2$)$_2$O—Me | CO$_2$Et | |
| 219 | SO$_2$Me | Cl | NH$_2$ | H | |
| 220 | SO$_2$Me | Cl | NHMe | H | |
| 221 | SO$_2$Me | Cl | NHEt | H | |
| 222 | SO$_2$Me | Cl | NH-n-Pr | H | |
| 223 | SO$_2$Me | Cl | NHAll | H | |
| 224 | SO$_2$Me | Cl | NH(CH$_2$)$_2$O—Me | H | |
| 225 | SO$_2$Me | Cl | N=CH—NMe$_2$ | H | |
| 226 | SO$_2$Me | Cl | NH$_2$ | CO$_2$Me | |
| 227 | SO$_2$Me | Cl | NHMe | CO$_2$Me | |
| 228 | SO$_2$Me | Cl | NHEt | CO$_2$Me | |
| 229 | SO$_2$Me | Cl | NH-n-Pr | CO$_2$Me | |
| 230 | SO$_2$Me | Cl | NHAll | CO$_2$Me | |
| 231 | SO$_2$Me | Cl | NH(CH$_2$)$_2$O—Me | CO$_2$Me | |
| 232 | SO$_2$Me | Cl | N=CH—NMe$_2$ | CO$_2$Me | |
| 233 | SO$_2$Me | Cl | NH$_2$ | CO$_2$Et | |
| 234 | SO$_2$Me | Cl | NHMe | CO$_2$Et | |
| 235 | SO$_2$Me | Cl | NHEt | CO$_2$Et | |
| 236 | SO$_2$Me | Cl | NH-n-Pr | CO$_2$Et | |
| 237 | SO$_2$Me | Cl | NHAll | CO$_2$Et | |
| 238 | SO$_2$Me | Cl | NH(CH$_2$)$_2$O—Me | CO$_2$Et | |
| 239 | SO$_2$Me | Cl | N=CH—NMe$_2$ | CO$_2$Et | |
| 240 | SO$_2$Me | Cl | NMe$_2$ | H | |
| 241 | SO$_2$Me | Cl | N(Me)Et | H | |
| 242 | SO$_2$Me | Cl | N(Me)-n-Pr | H | |
| 243 | SO$_2$Me | Cl | N(Me)All | H | |
| 244 | SO$_2$Me | Cl | N(Me)(CH$_2$)$_2$O—Me | H | |
| 245 | SO$_2$Me | Cl | NMe$_2$ | CO$_2$Me | |
| 246 | SO$_2$Me | Cl | N(Me)Et | CO$_2$Me | |
| 247 | SO$_2$Me | Cl | N(Me)-n-Pr | CO$_2$Me | |
| 248 | SO$_2$Me | Cl | N(Me)All | CO$_2$Me | |
| 249 | SO$_2$Me | Cl | N(Me)(CH$_2$)$_2$O—Me | CO$_2$Me | |
| 250 | SO$_2$Me | Cl | NMe$_2$ | CO$_2$Et | |
| 251 | SO$_2$Me | Cl | N(Me)Et | CO$_2$Et | |
| 252 | SO$_2$Me | Cl | N(Me)-n-Pr | CO$_2$Et | |
| 253 | SO$_2$Me | Cl | N(Me)All | CO$_2$Et | |
| 254 | SO$_2$Me | Cl | N(Me)(CH$_2$)$_2$O—Me | CO$_2$Et | |
| 255 | SO$_2$Me | OMe | NH$_2$ | H | |
| 256 | SO$_2$Me | OMe | NHMe | H | |
| 257 | SO$_2$Me | OMe | NHEt | H | |

TABLE A-continued

Compounds of the formula (I) according to the invention

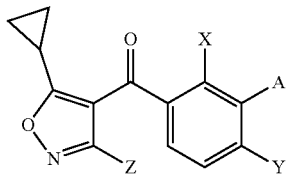

(I)

| No. | X | Y | A | Z | Physical data: $^1$H NMR: δ [CDCl$_3$] |
|---|---|---|---|---|---|
| 258 | SO$_2$Me | OMe | NH-n-Pr | H | |
| 259 | SO$_2$Me | OMe | NHAll | H | |
| 260 | SO$_2$Me | OMe | NH(CH$_2$)$_2$O—Me | H | |
| 261 | SO$_2$Me | OMe | N=CH—NMe$_2$ | H | |
| 262 | SO$_2$Me | OMe | NH$_2$ | CO$_2$Me | |
| 263 | SO$_2$Me | OMe | NHMe | CO$_2$Me | |
| 264 | SO$_2$Me | OMe | NHEt | CO$_2$Me | |
| 265 | SO$_2$Me | OMe | NH-n-Pr | CO$_2$Me | |
| 266 | SO$_2$Me | OMe | NHAll | CO$_2$Me | |
| 267 | SO$_2$Me | OMe | NH(CH$_2$)$_2$O—Me | CO$_2$Me | |
| 268 | SO$_2$Me | OMe | N=CH—NMe$_2$ | CO$_2$Me | |
| 269 | SO$_2$Me | OMe | NH$_2$ | CO$_2$Et | |
| 270 | SO$_2$Me | OMe | NHMe | CO$_2$Et | |
| 271 | SO$_2$Me | OMe | NHEt | CO$_2$Et | |
| 272 | SO$_2$Me | OMe | NH-n-Pr | CO$_2$Et | |
| 273 | SO$_2$Me | OMe | NHAll | CO$_2$Et | |
| 274 | SO$_2$Me | OMe | NH(CH$_2$)$_2$O—Me | CO$_2$Et | |
| 275 | SO$_2$Me | OMe | N=CH—NMe$_2$ | CO$_2$Et | |
| 276 | SO$_2$Me | OMe | NMe$_2$ | H | |
| 277 | SO$_2$Me | OMe | N(Me)Et | H | |
| 278 | SO$_2$Me | OMe | N(Me)-n-Pr | H | |
| 279 | SO$_2$Me | OMe | N(Me)All | H | |
| 280 | SO$_2$Me | OMe | N(Me)(CH$_2$)$_2$O—Me | H | |
| 281 | SO$_2$Me | OMe | NMe$_2$ | CO$_2$Me | |
| 282 | SO$_2$Me | OMe | N(Me)Et | CO$_2$Me | |
| 283 | SO$_2$Me | OMe | N(Me)-n-Pr | CO$_2$Me | |
| 284 | SO$_2$Me | OMe | N(Me)All | CO$_2$Me | |
| 285 | SO$_2$Me | OMe | N(Me)(CH$_2$)$_2$O—Me | CO$_2$Me | |
| 286 | SO$_2$Me | OMe | NMe$_2$ | CO$_2$Et | |
| 287 | SO$_2$Me | OMe | N(Me)Et | CO$_2$Et | |
| 288 | SO$_2$Me | OMe | N(Me)-n-Pr | CO$_2$Et | |
| 289 | SO$_2$Me | OMe | N(Me)All | CO$_2$Et | |
| 290 | SO$_2$Me | OMe | N(Me)(CH$_2$)$_2$O—Me | CO$_2$Et | |
| 291 | CF$_3$ | SO$_2$Me | NH$_2$ | H | |
| 292 | CF$_3$ | SO$_2$Me | NHMe | H | |
| 293 | CF$_3$ | SO$_2$Me | NHEt | H | |
| 294 | CF$_3$ | SO$_2$Me | NH-n-Pr | H | |
| 295 | CF$_3$ | SO$_2$Me | NHAll | H | |
| 296 | CF$_3$ | SO$_2$Me | NH(CH$_2$)$_2$O—Me | H | |
| 297 | CF$_3$ | SO$_2$Me | N=CH—NMe$_2$ | H | |
| 298 | CF$_3$ | SO$_2$Me | NH$_2$ | CO$_2$Me | |
| 299 | CF$_3$ | SO$_2$Me | NHMe | CO$_2$Me | |
| 300 | CF$_3$ | SO$_2$Me | NHEt | CO$_2$Me | |
| 301 | CF$_3$ | SO$_2$Me | NH-n-Pr | CO$_2$Me | |
| 302 | CF$_3$ | SO$_2$Me | NHAll | CO$_2$Me | |
| 303 | CF$_3$ | SO$_2$Me | NH(CH$_2$)$_2$O—Me | CO$_2$Me | |
| 304 | CF$_3$ | SO$_2$Me | N=CH—NMe$_2$ | CO$_2$Me | |
| 305 | CF$_3$ | SO$_2$Me | NH$_2$ | CO$_2$Et | |
| 306 | CF$_3$ | SO$_2$Me | NHMe | CO$_2$Et | |
| 307 | CF$_3$ | SO$_2$Me | NHEt | CO$_2$Et | |
| 308 | CF$_3$ | SO$_2$Me | NH-n-Pr | CO$_2$Et | |
| 309 | CF$_3$ | SO$_2$Me | NHAll | CO$_2$Et | |
| 310 | CF$_3$ | SO$_2$Me | NH(CH$_2$)$_2$O—Me | CO$_2$Et | |
| 311 | CF$_3$ | SO$_2$Me | N=CH—NMe$_2$ | CO$_2$Et | |
| 312 | CF$_3$ | SO$_2$Me | NMe$_2$ | H | |
| 313 | CF$_3$ | SO$_2$Me | N(Me)Et | H | |
| 314 | CF$_3$ | SO$_2$Me | N(Me)-n-Pr | H | |
| 315 | CF$_3$ | SO$_2$Me | N(Me)All | H | |
| 316 | CF$_3$ | SO$_2$Me | N(Me)(CH$_2$)$_2$O—Me | H | |
| 317 | CF$_3$ | SO$_2$Me | NMe$_2$ | CO$_2$Me | |
| 318 | CF$_3$ | SO$_2$Me | N(Me)Et | CO$_2$Me | |
| 319 | CF$_3$ | SO$_2$Me | N(Me)-n-Pr | CO$_2$Me | |
| 320 | CF$_3$ | SO$_2$Me | N(Me)All | CO$_2$Me | |
| 321 | CF$_3$ | SO$_2$Me | N(Me)(CH$_2$)$_2$O—Me | CO$_2$Me | |

TABLE A-continued

Compounds of the formula (I) according to the invention (I)

| No. | X | Y | A | Z | Physical data: $^1$H NMR: δ [CDCl$_3$] |
|---|---|---|---|---|---|
| 322 | CF$_3$ | SO$_2$Me | NMe$_2$ | CO$_2$Et | |
| 323 | CF$_3$ | SO$_2$Me | N(Me)Et | CO$_2$Et | |
| 324 | CF$_3$ | SO$_2$Me | N(Me)-n-Pr | CO$_2$Et | |
| 325 | CF$_3$ | SO$_2$Me | N(Me)All | CO$_2$Et | |
| 326 | CF$_3$ | SO$_2$Me | N(Me)(CH$_2$)$_2$O—Me | CO$_2$Et | |
| 327 | CF$_3$ | Cl | NH$_2$ | H | |
| 328 | CF$_3$ | Cl | NHMe | H | |
| 329 | CF$_3$ | Cl | NHEt | H | |
| 330 | CF$_3$ | Cl | NH-n-Pr | H | |
| 331 | CF$_3$ | Cl | NHAll | H | |
| 332 | CF$_3$ | Cl | NH(CH$_2$)$_2$O—Me | H | |
| 333 | CF$_3$ | Cl | N=CH—NMe$_2$ | H | |
| 334 | CF$_3$ | Cl | NH$_2$ | CO$_2$Me | |
| 335 | CF$_3$ | Cl | NHMe | CO$_2$Me | |
| 336 | CF$_3$ | Cl | NHEt | CO$_2$Me | |
| 337 | CF$_3$ | Cl | NH-n-Pr | CO$_2$Me | |
| 338 | CF$_3$ | Cl | NHAll | CO$_2$Me | |
| 339 | CF$_3$ | Cl | NH(CH$_2$)$_2$O—Me | CO$_2$Me | |
| 340 | CF$_3$ | Cl | N=CH—NMe$_2$ | CO$_2$Me | |
| 341 | CF$_3$ | Cl | NH$_2$ | CO$_2$Et | |
| 342 | CF$_3$ | Cl | NHMe | CO$_2$Et | |
| 343 | CF$_3$ | Cl | NHEt | CO$_2$Et | |
| 344 | CF$_3$ | Cl | NH-n-Pr | CO$_2$Et | |
| 345 | CF$_3$ | Cl | NHAll | CO$_2$Et | |
| 346 | CF$_3$ | Cl | NH(CH$_2$)$_2$O—Me | CO$_2$Et | |
| 347 | CF$_3$ | Cl | N=CH—NMe$_2$ | CO$_2$Et | |
| 348 | CF$_3$ | Cl | NMe$_2$ | H | |
| 349 | CF$_3$ | Cl | N(Me)Et | H | |
| 350 | CF$_3$ | Cl | N(Me)-n-Pr | H | |
| 351 | CF$_3$ | Cl | N(Me)All | H | |
| 352 | CF$_3$ | Cl | N(Me)(CH$_2$)$_2$O—Me | H | |
| 353 | CF$_3$ | Cl | NMe$_2$ | CO$_2$Me | |
| 354 | CF$_3$ | Cl | N(Me)Et | CO$_2$Me | |
| 355 | CF$_3$ | Cl | N(Me)-n-Pr | CO$_2$Me | |
| 356 | CF$_3$ | Cl | N(Me)All | CO$_2$Me | |
| 357 | CF$_3$ | Cl | N(Me)(CH$_2$)$_2$O—Me | CO$_2$Me | |
| 358 | CF$_3$ | Cl | NMe$_2$ | CO$_2$Et | |
| 359 | CF$_3$ | Cl | N(Me)Et | CO$_2$Et | |
| 360 | CF$_3$ | Cl | N(Me)-n-Pr | CO$_2$Et | |
| 361 | CF$_3$ | Cl | N(Me)All | CO$_2$Et | |
| 362 | CF$_3$ | Cl | N(Me)(CH$_2$)$_2$O—Me | CO$_2$Et | |
| 363 | CF$_3$ | OMe | NH$_2$ | H | |
| 364 | CF$_3$ | OMe | NHMe | H | |
| 365 | CF$_3$ | OMe | NHEt | H | |
| 366 | CF$_3$ | OMe | NH-n-Pr | H | |
| 367 | CF$_3$ | OMe | NHAll | H | |
| 368 | CF$_3$ | OMe | NH(CH$_2$)$_2$O—Me | H | |
| 369 | CF$_3$ | OMe | N=CH—NMe$_2$ | H | |
| 370 | CF$_3$ | OMe | NH$_2$ | CO$_2$Me | |
| 371 | CF$_3$ | OMe | NHMe | CO$_2$Me | |
| 372 | CF$_3$ | OMe | NHEt | CO$_2$Me | |
| 373 | CF$_3$ | OMe | NH-n-Pr | CO$_2$Me | |
| 374 | CF$_3$ | OMe | NHAll | CO$_2$Me | |
| 375 | CF$_3$ | OMe | NH(CH$_2$)$_2$O—Me | CO$_2$Me | |
| 376 | CF$_3$ | OMe | N=CH—NMe$_2$ | CO$_2$Me | |
| 377 | CF$_3$ | OMe | NH$_2$ | CO$_2$Et | |
| 378 | CF$_3$ | OMe | NHMe | CO$_2$Et | |
| 379 | CF$_3$ | OMe | NHEt | CO$_2$Et | |
| 380 | CF$_3$ | OMe | NH-n-Pr | CO$_2$Et | |
| 381 | CF$_3$ | OMe | NHAll | CO$_2$Et | |
| 382 | CF$_3$ | OMe | NH(CH$_2$)$_2$O—Me | CO$_2$Et | |
| 383 | CF$_3$ | OMe | N=CH—NMe$_2$ | CO$_2$Et | |
| 384 | CF$_3$ | OMe | NMe$_2$ | H | |
| 385 | CF$_3$ | OMe | N(Me)Et | H | |

TABLE A-continued

Compounds of the formula (I) according to the invention (I)

| No. | X | Y | A | Z | Physical data: $^1$H NMR: δ [CDCl$_3$] |
|---|---|---|---|---|---|
| 386 | CF$_3$ | OMe | N(Me)-n-Pr | H | |
| 387 | CF$_3$ | OMe | N(Me)All | H | |
| 388 | CF$_3$ | OMe | N(Me)(CH$_2$)$_2$O—Me | H | |
| 389 | CF$_3$ | OMe | NMe$_2$ | CO$_2$Me | |
| 390 | CF$_3$ | OMe | N(Me)Et | CO$_2$Me | |
| 391 | CF$_3$ | OMe | N(Me)-n-Pr | CO$_2$Me | |
| 392 | CF$_3$ | OMe | N(Me)All | CO$_2$Me | |
| 393 | CF$_3$ | OMe | N(Me)(CH$_2$)$_2$O—Me | CO$_2$Me | |
| 394 | CF$_3$ | OMe | NMe$_2$ | CO$_2$Et | |
| 395 | CF$_3$ | OMe | N(Me)Et | CO$_2$Et | |
| 396 | CF$_3$ | OMe | N(Me)-n-Pr | CO$_2$Et | |
| 397 | CF$_3$ | OMe | N(Me)All | CO$_2$Et | |
| 398 | CF$_3$ | OMe | N(Me)(CH$_2$)$_2$O—Me | CO$_2$Et | |
| 399 | Cl | SO$_2$Me | NH$_2$ | H | 8.18 (s, 1H), 7.81 (d, 1H), 6.83 (d, 1H), 5.77 (br, 2H), 3.12 (s, 3H), 2.66-2.75 (m, 1H), 1.36-1.41 (m, 2H), 1.24-1.31 (m, 2H) |
| 400 | Cl | SO$_2$Me | NHMe | H | |
| 401 | Cl | SO$_2$Me | NHEt | H | |
| 402 | Cl | SO$_2$Me | NH-n-Pr | H | 8.18 (s, 1H), 7.89 (d,1H), 6.93 (d, 1H), 3.51 (t, 2H), 3.14 (s, 3H), 2.61-2.72 (m, 1H), 1.64-1.78 (m, 2H), 1.34-1.42 (m, 2H), 1.22-1.33 (m, 2H), 1.03 (t, 3H) |
| 403 | Cl | SO$_2$Me | NHAll | H | |
| 404 | Cl | SO$_2$Me | NH(CH$_2$)$_2$O—Me | H | |
| 405 | Cl | SO$_2$Me | N=CH—NMe$_2$ | H | 8.16 (s, 1H), 8.03 (d, 1H), 7.45 (s, 1H), 7.09 (d, 1H), 3.32 (s,3H), 3.13 (s, 3H), 3.09 (s, 3H), 2.69-2.82 (m, 1H), 1.35-1.44 (m, 2H), 1.23-1.34 (m, 2H) |
| 406 | Cl | SO$_2$Me | NH$_2$ | CO$_2$Me | |
| 407 | Cl | SO$_2$Me | NHMe | CO$_2$Me | |
| 408 | Cl | SO$_2$Me | NHEt | CO$_2$Me | |
| 409 | Cl | SO$_2$Me | NH-n-Pr | CO$_2$Me | |
| 410 | Cl | SO$_2$Me | NHAll | CO$_2$Me | |
| 411 | Cl | SO$_2$Me | NH(CH$_2$)$_2$O—Me | CO$_2$Me | |
| 412 | Cl | SO$_2$Me | N=CH—NMe$_2$ | CO$_2$Me | |
| 413 | Cl | SO$_2$Me | NH$_2$ | CO$_2$Et | |
| 414 | Cl | SO$_2$Me | NHMe | CO$_2$Et | |
| 415 | Cl | SO$_2$Me | NHEt | CO$_2$Et | |
| 416 | Cl | SO$_2$Me | NH-n-Pr | CO$_2$Et | |
| 417 | Cl | SO$_2$Me | NHAll | CO$_2$Et | |
| 418 | Cl | SO$_2$Me | NH(CH$_2$)$_2$O—Me | CO$_2$Et | |
| 419 | Cl | SO$_2$Me | N=CH—NMe$_2$ | CO$_2$Et | |
| 420 | Cl | SO$_2$Me | NMe$_2$ | H | |
| 421 | Cl | SO$_2$Me | N(Me)Et | H | |
| 422 | Cl | SO$_2$Me | N(Me)-n-Pr | H | |
| 423 | Cl | SO$_2$Me | N(Me)All | H | |
| 424 | Cl | SO$_2$Me | N(Me)(CH$_2$)$_2$O—Me | H | |
| 425 | Cl | SO$_2$Me | NMe$_2$ | CO$_2$Me | |
| 426 | Cl | SO$_2$Me | N(Me)Et | CO$_2$Me | |
| 427 | Cl | SO$_2$Me | N(Me)-n-Pr | CO$_2$Me | |
| 428 | Cl | SO$_2$Me | N(Me)All | CO$_2$Me | |
| 429 | Cl | SO$_2$Me | N(Me)(CH$_2$)$_2$O—Me | CO$_2$Me | |
| 430 | Cl | SO$_2$Me | NMe$_2$ | CO$_2$Et | |
| 431 | Cl | SO$_2$Me | N(Me)Et | CO$_2$Et | |
| 432 | Cl | SO$_2$Me | N(Me)-n-Pr | CO$_2$Et | |
| 433 | Cl | SO$_2$Me | N(Me)All | CO$_2$Et | |
| 434 | Cl | SO$_2$Me | N(Me)(CH$_2$)$_2$O—Me | CO$_2$Et | |
| 435 | Cl | CF$_3$ | NH$_2$ | H | |
| 436 | Cl | CF$_3$ | NHMe | H | |
| 437 | Cl | CF$_3$ | NHEt | H | |
| 438 | Cl | CF$_3$ | NH-n-Pr | H | |
| 439 | Cl | CF$_3$ | NHAll | H | |
| 440 | Cl | CF$_3$ | NH(CH$_2$)$_2$O—Me | H | |

TABLE A-continued

Compounds of the formula (I) according to the invention (I)

| No. | X | Y | A | Z | Physical data: $^1$H NMR: δ [CDCl$_3$] |
|---|---|---|---|---|---|
| 441 | Cl | CF$_3$ | N=CH—NMe$_2$ | H | |
| 442 | Cl | CF$_3$ | NH$_2$ | CO$_2$Me | |
| 443 | Cl | CF$_3$ | NHMe | CO$_2$Me | |
| 444 | Cl | CF$_3$ | NHEt | CO$_2$Me | |
| 445 | Cl | CF$_3$ | NH-n-Pr | CO$_2$Me | |
| 446 | Cl | CF$_3$ | NHAll | CO$_2$Me | |
| 447 | Cl | CF$_3$ | NH(CH$_2$)$_2$O—Me | CO$_2$Me | |
| 448 | Cl | CF$_3$ | N=CH—NMe$_2$ | CO$_2$Me | |
| 449 | Cl | CF$_3$ | NH$_2$ | CO$_2$Et | |
| 450 | Cl | CF$_3$ | NHMe | CO$_2$Et | |
| 451 | Cl | CF$_3$ | NHEt | CO$_2$Et | |
| 452 | Cl | CF$_3$ | NH-n-Pr | CO$_2$Et | |
| 453 | Cl | CF$_3$ | NHAll | CO$_2$Et | |
| 454 | Cl | CF$_3$ | NH(CH$_2$)$_2$O—Me | CO$_2$Et | |
| 455 | Cl | CF$_3$ | N=CH—NMe$_2$ | CO$_2$Et | |
| 456 | Cl | CF$_3$ | NMe$_2$ | H | |
| 457 | Cl | CF$_3$ | N(Me)Et | H | |
| 458 | Cl | CF$_3$ | N(Me)-n-Pr | H | |
| 459 | Cl | CF$_3$ | N(Me)All | H | |
| 460 | Cl | CF$_3$ | N(Me)(CH$_2$)$_2$O—Me | H | |
| 461 | Cl | CF$_3$ | NMe$_2$ | CO$_2$Me | |
| 462 | Cl | CF$_3$ | N(Me)Et | CO$_2$Me | |
| 463 | Cl | CF$_3$ | N(Me)-n-Pr | CO$_2$Me | |
| 464 | Cl | CF$_3$ | N(Me)All | CO$_2$Me | |
| 465 | Cl | CF$_3$ | N(Me)(CH$_2$)$_2$O—Me | CO$_2$Me | |
| 466 | Cl | CF$_3$ | NMe$_2$ | CO$_2$Et | |
| 467 | Cl | CF$_3$ | N(Me)Et | CO$_2$Et | |
| 468 | Cl | CF$_3$ | N(Me)-n-Pr | CO$_2$Et | |
| 469 | Cl | CF$_3$ | N(Me)All | CO$_2$Et | |
| 470 | Cl | CF$_3$ | N(Me)(CH$_2$)$_2$O—Me | CO$_2$Et | |
| 471 | Cl | Cl | NH$_2$ | H | |
| 472 | Cl | Cl | NHMe | H | |
| 473 | Cl | Cl | NHEt | H | |
| 474 | Cl | Cl | NH-n-Pr | H | |
| 475 | Cl | Cl | NHAll | H | |
| 476 | Cl | Cl | NH(CH$_2$)$_2$O—Me | H | |
| 477 | Cl | Cl | N=CH—NMe$_2$ | H | |
| 478 | Cl | Cl | NH$_2$ | CO$_2$Me | |
| 479 | Cl | Cl | NHMe | CO$_2$Me | |
| 480 | Cl | Cl | NHEt | CO$_2$Me | |
| 481 | Cl | Cl | NH-n-Pr | CO$_2$Me | |
| 482 | Cl | Cl | NHAll | CO$_2$Me | |
| 483 | Cl | Cl | NH(CH$_2$)$_2$O—Me | CO$_2$Me | |
| 484 | Cl | Cl | N=CH—NMe$_2$ | CO$_2$Me | |
| 485 | Cl | Cl | NH$_2$ | CO$_2$Et | |
| 486 | Cl | Cl | NHMe | CO$_2$Et | |
| 487 | Cl | Cl | NHEt | CO$_2$Et | |
| 488 | Cl | Cl | NH-n-Pr | CO$_2$Et | |
| 489 | Cl | Cl | NHAll | CO$_2$Et | |
| 490 | Cl | Cl | NH(CH$_2$)$_2$O—Me | CO$_2$Et | |
| 491 | Cl | Cl | N=CH—NMe$_2$ | CO$_2$Et | |
| 492 | Cl | Cl | NMe$_2$ | H | |
| 493 | Cl | Cl | N(Me)Et | H | |
| 494 | Cl | Cl | N(Me)-n-Pr | H | |
| 495 | Cl | Cl | N(Me)All | H | |
| 496 | Cl | Cl | N(Me)(CH$_2$)$_2$O—Me | H | |
| 497 | Cl | Cl | NMe$_2$ | CO$_2$Me | |
| 498 | Cl | Cl | N(Me)Et | CO$_2$Me | |
| 499 | Cl | Cl | N(Me)-n-Pr | CO$_2$Me | |
| 500 | Cl | Cl | N(Me)All | CO$_2$Me | |
| 501 | Cl | Cl | N(Me)(CH$_2$)$_2$O—Me | CO$_2$Me | |
| 502 | Cl | Cl | NMe$_2$ | CO$_2$Et | |
| 503 | Cl | Cl | N(Me)Et | CO$_2$Et | |
| 504 | Cl | Cl | N(Me)-n-Pr | CO$_2$Et | |

TABLE A-continued

Compounds of the formula (I) according to the invention

| No. | X | Y | A | Z | Physical data: $^1$H NMR: δ [CDCl$_3$] |
|---|---|---|---|---|---|
| 505 | Cl | Cl | N(Me)All | CO$_2$Et | |
| 506 | Cl | Cl | N(Me)(CH$_2$)$_2$O—Me | CO$_2$Et | |
| 507 | Cl | OMe | NH$_2$ | H | |
| 508 | Cl | OMe | NHMe | H | |
| 509 | Cl | OMe | NHEt | H | |
| 510 | Cl | OMe | NH-n-Pr | H | |
| 511 | Cl | OMe | NHAll | H | |
| 512 | Cl | OMe | NH(CH$_2$)$_2$O—Me | H | |
| 513 | Cl | OMe | N=CH—NMe$_2$ | H | |
| 514 | Cl | OMe | NH$_2$ | CO$_2$Me | |
| 515 | Cl | OMe | NHMe | CO$_2$Me | |
| 516 | Cl | OMe | NHEt | CO$_2$Me | |
| 517 | Cl | OMe | NH-n-Pr | CO$_2$Me | |
| 518 | Cl | OMe | NHAll | CO$_2$Me | |
| 519 | Cl | OMe | NH(CH$_2$)$_2$O—Me | CO$_2$Me | |
| 520 | Cl | OMe | N=CH—NMe$_2$ | CO$_2$Me | |
| 521 | Cl | OMe | NH$_2$ | CO$_2$Et | |
| 522 | Cl | OMe | NHMe | CO$_2$Et | |
| 523 | Cl | OMe | NHEt | CO$_2$Et | |
| 524 | Cl | OMe | NH-n-Pr | CO$_2$Et | |
| 525 | Cl | OMe | NHAll | CO$_2$Et | |
| 526 | Cl | OMe | NH(CH$_2$)$_2$O—Me | CO$_2$Et | |
| 527 | Cl | OMe | N=CH—NMe$_2$ | CO$_2$Et | |
| 528 | Cl | OMe | NMe$_2$ | H | |
| 529 | Cl | OMe | N(Me)Et | H | |
| 530 | Cl | OMe | N(Me)-n-Pr | H | |
| 531 | Cl | OMe | N(Me)All | H | |
| 532 | Cl | OMe | N(Me)(CH$_2$)$_2$O—Me | H | |
| 533 | Cl | OMe | NMe$_2$ | CO$_2$Me | |
| 534 | Cl | OMe | N(Me)Et | CO$_2$Me | |
| 535 | Cl | OMe | N(Me)-n-Pr | CO$_2$Me | |
| 536 | Cl | OMe | N(Me)All | CO$_2$Me | |
| 537 | Cl | OMe | N(Me)(CH$_2$)$_2$O—Me | CO$_2$Me | |
| 538 | Cl | OMe | NMe$_2$ | CO$_2$Et | |
| 539 | Cl | OMe | N(Me)Et | CO$_2$Et | |
| 540 | Cl | OMe | N(Me)-n-Pr | CO$_2$Et | |
| 541 | Cl | OMe | N(Me)All | CO$_2$Et | |
| 542 | Cl | OMe | N(Me)(CH$_2$)$_2$O—Me | CO$_2$Et | |
| 543 | OMe | SO$_2$Me | NH$_2$ | H | 8.24 (s, 1H), 7.60 (d, 1H), 6.80 (d, 1H), 5.48 (br, 2H), 3.78 (s, 3H), 3.12 (s, 3H), 2.75-2.85 (m, 1H), 1.35-1.40 (m, 2H), 1.22-1.35 (m, 2H) |
| 544 | OMe | SO$_2$Me | NHMe | H | 8.25 (s, 1H), 7.66 (d, 1H), 6.80 (d, 1H), 5.95 (br, 1H), 3.68 (s, 3H), 3.15 (d, 3H), 3.08 (s, 3H), 2.78-2.85 (m, 1H), 1.35-1.40 (m, 2H), 1.25-1.30 (m, 2H) |
| 545 | OMe | SO$_2$Me | NHEt | H | |
| 546 | OMe | SO$_2$Me | NH-n-Pr | H | |
| 547 | OMe | SO$_2$Me | NHAll | H | |
| 548 | OMe | SO$_2$Me | NH(CH$_2$)$_2$O—Me | H | |
| 549 | OMe | SO$_2$Me | N=CH—NMe$_2$ | H | 7.80 (s, 1H), 7.65 (s, 1H), 7.35 (d, 1H), 6.40 (s, 1H), 3.65 (s, 3H), 3.35 (s, 3H), 3.08 (s, 3H), 3.05 (s, 3H), 1.75-1.85 (s, 1H), 1.20-1.25 (m, 2H), 0.98-1.05 (m, 2H) |
| 550 | OMe | SO$_2$Me | NH$_2$ | CO$_2$Me | |
| 551 | OMe | SO$_2$Me | NHMe | CO$_2$Me | |
| 552 | OMe | SO$_2$Me | NHEt | CO$_2$Me | |
| 553 | OMe | SO$_2$Me | NH-n-Pr | CO$_2$Me | |
| 554 | OMe | SO$_2$Me | NHAll | CO$_2$Me | |
| 555 | OMe | SO$_2$Me | NH(CH$_2$)$_2$O—Me | CO$_2$Me | |
| 556 | OMe | SO$_2$Me | N=CH—NMe$_2$ | CO$_2$Me | |
| 557 | OMe | SO$_2$Me | NH$_2$ | CO$_2$Et | |
| 558 | OMe | SO$_2$Me | NHMe | CO$_2$Et | |

TABLE A-continued

Compounds of the formula (I) according to the invention

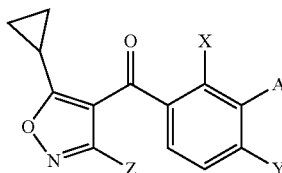

(I)

| No. | X | Y | A | Z | Physical data: $^1$H NMR: δ [CDCl$_3$] |
|---|---|---|---|---|---|
| 559 | OMe | SO$_2$Me | NHEt | CO$_2$Et | |
| 560 | OMe | SO$_2$Me | NH-n-Pr | CO$_2$Et | |
| 561 | OMe | SO$_2$Me | NHAll | CO$_2$Et | |
| 562 | OMe | SO$_2$Me | NH(CH$_2$)$_2$O—Me | CO$_2$Et | |
| 563 | OMe | SO$_2$Me | N═CH—NMe$_2$ | CO$_2$Et | |
| 564 | OMe | SO$_2$Me | NMe$_2$ | H | 8.20 (s, 1H), 7.90 (d, 1H), 7.40 (d, 1H), 3.78 (s, 3H), 3.35 (d,3H), 3.90 (s, 6H), 2.78-2.85 (m, 1H), 1.38-1.42 (m, 2H), 1.25-1.32 (m, 2H) |
| 565 | OMe | SO$_2$Me | N(Me)Et | H | |
| 566 | OMe | SO$_2$Me | N(Me)-n-Pr | H | |
| 567 | OMe | SO$_2$Me | N(Me)All | H | |
| 568 | OMe | SO$_2$Me | N(Me)(CH$_2$)$_2$O—Me | H | |
| 569 | OMe | SO$_2$Me | NMe$_2$ | CO$_2$Me | |
| 570 | OMe | SO$_2$Me | N(Me)Et | CO$_2$Me | |
| 571 | OMe | SO$_2$Me | N(Me)-n-Pr | CO$_2$Me | |
| 572 | OMe | SO$_2$Me | N(Me)All | CO$_2$Me | |
| 573 | OMe | SO$_2$Me | N(Me)(CH$_2$)$_2$O—Me | CO$_2$Me | |
| 574 | OMe | SO$_2$Me | NMe$_2$ | CO$_2$Et | |
| 575 | OMe | SO$_2$Me | N(Me)Et | CO$_2$Et | |
| 576 | OMe | SO$_2$Me | N(Me)-n-Pr | CO$_2$Et | |
| 577 | OMe | SO$_2$Me | N(Me)All | CO$_2$Et | |
| 578 | OMe | SO$_2$Me | N(Me)(CH$_2$)$_2$O—Me | CO$_2$Et | |
| 579 | OMe | CF$_3$ | NH$_2$ | H | |
| 580 | OMe | CF$_3$ | NHMe | H | |
| 581 | OMe | CF$_3$ | NHEt | H | |
| 582 | OMe | CF$_3$ | NH-n-Pr | H | |
| 583 | OMe | CF$_3$ | NHAll | H | |
| 584 | OMe | CF$_3$ | NH(CH$_2$)$_2$O—Me | H | |
| 585 | OMe | CF$_3$ | N═CH—NMe$_2$ | H | |
| 586 | OMe | CF$_3$ | NH$_2$ | CO$_2$Me | |
| 587 | OMe | CF$_3$ | NHMe | CO$_2$Me | |
| 588 | OMe | CF$_3$ | NHEt | CO$_2$Me | |
| 589 | OMe | CF$_3$ | NH-n-Pr | CO$_2$Me | |
| 590 | OMe | CF$_3$ | NHAll | CO$_2$Me | |
| 591 | OMe | CF$_3$ | NH(CH$_2$)$_2$O—Me | CO$_2$Me | |
| 592 | OMe | CF$_3$ | N═CH—NMe$_2$ | CO$_2$Me | |
| 593 | OMe | CF$_3$ | NH$_2$ | CO$_2$Et | |
| 594 | OMe | CF$_3$ | NHMe | CO$_2$Et | |
| 595 | OMe | CF$_3$ | NHEt | CO$_2$Et | |
| 596 | OMe | CF$_3$ | NH-n-Pr | CO$_2$Et | |
| 597 | OMe | CF$_3$ | NHAll | CO$_2$Et | |
| 598 | OMe | CF$_3$ | NH(CH$_2$)$_2$O—Me | CO$_2$Et | |
| 599 | OMe | CF$_3$ | N═CH—NMe$_2$ | CO$_2$Et | |
| 600 | OMe | CF$_3$ | NMe$_2$ | H | |
| 601 | OMe | CF$_3$ | N(Me)Et | H | |
| 602 | OMe | CF$_3$ | N(Me)-n-Pr | H | |
| 603 | OMe | CF$_3$ | N(Me)All | H | |
| 604 | OMe | CF$_3$ | N(Me)(CH$_2$)$_2$O—Me | H | |
| 605 | OMe | CF$_3$ | NMe$_2$ | CO$_2$Me | |
| 606 | OMe | CF$_3$ | N(Me)Et | CO$_2$Me | |
| 607 | OMe | CF$_3$ | N(Me)-n-Pr | CO$_2$Me | |
| 608 | OMe | CF$_3$ | N(Me)All | CO$_2$Me | |
| 609 | OMe | CF$_3$ | N(Me)(CH$_2$)$_2$O—Me | CO$_2$Me | |
| 610 | OMe | CF$_3$ | NMe$_2$ | CO$_2$Et | |
| 611 | OMe | CF$_3$ | N(Me)Et | CO$_2$Et | |
| 612 | OMe | CF$_3$ | N(Me)-n-Pr | CO$_2$Et | |
| 613 | OMe | CF$_3$ | N(Me)All | CO$_2$Et | |
| 614 | OMe | CF$_3$ | N(Me)(CH$_2$)$_2$O—Me | CO$_2$Et | |
| 615 | OMe | Cl | NH$_2$ | H | 8.24 (s, 1H), 7.15 (d, 1H), 6.76 (d, 1H), 4.38 (br, 2H), 3.75 (s, 3H), 2.75-2.82 (m, 1H), 1.30-1.38 (m, 2H), 1.20-1.30 (m, 2H) |

TABLE A-continued

Compounds of the formula (I) according to the invention (I)

| No. | X | Y | A | Z | Physical data:<br>$^1$H NMR: δ [CDCl$_3$] |
|---|---|---|---|---|---|
| 616 | OMe | Cl | NHMe | H | 8.22 (s, 1H), 7.15 (d, 1H), 6.80 (d, 1H), 3.70 (s, 3H), 3.05 (s, 3H), 2.75-2.82 (m, 1H), 1.30-1.38 (m, 2H), 1.20-1.30 (m, 2H) |
| 617 | OMe | Cl | NHEt | H | |
| 618 | OMe | Cl | NH-n-Pr | H | |
| 619 | OMe | Cl | NHAll | H | |
| 620 | OMe | Cl | NH(CH$_2$)$_2$O—Me | H | |
| 621 | OMe | Cl | N=CH—NMe$_2$ | H | 7.42 (s, 1H), 7.12 (s,1H), 7.05 (d, 1H), 3.75 (s, 3H), 2.85 (s, 6H), 2.0-2.10 (s, 1H), 0.95-1.0 (m, 2H), 0.65-0.70 (m, 2H) |
| 622 | OMe | Cl | NH$_2$ | CO$_2$Me | |
| 623 | OMe | Cl | NHMe | CO$_2$Me | |
| 624 | OMe | Cl | NHEt | CO$_2$Me | |
| 625 | OMe | Cl | NH-n-Pr | CO$_2$Me | |
| 626 | OMe | Cl | NHAll | CO$_2$Me | |
| 627 | OMe | Cl | NH(CH$_2$)$_2$O—Me | CO$_2$Me | |
| 628 | OMe | Cl | N=CH—NMe$_2$ | CO$_2$Me | |
| 629 | OMe | Cl | NH$_2$ | CO$_2$Et | |
| 630 | OMe | Cl | NHMe | CO$_2$Et | |
| 631 | OMe | Cl | NHEt | CO$_2$Et | |
| 632 | OMe | Cl | NH-n-Pr | CO$_2$Et | |
| 633 | OMe | Cl | NHAll | CO$_2$Et | |
| 634 | OMe | Cl | NH(CH$_2$)$_2$O—Me | CO$_2$Et | |
| 635 | OMe | Cl | N=CH—NMe$_2$ | CO$_2$Et | |
| 636 | OMe | Cl | NMe$_2$ | H | 8.22 (s, 1H), 7.20 (d, 1H), 7.05 (d, 1H), 3.68 (s, 3H), 2.92 (s, 6H), 2.75-2.80 (m, 1H), 1.30-1.38 (m, 2H), 1.20-1.30 (m, 2H) |
| 637 | OMe | Cl | N(Me)Et | H | |
| 638 | OMe | Cl | N(Me)-n-Pr | H | |
| 639 | OMe | Cl | N(Me)All | H | |
| 640 | OMe | Cl | N(Me)(CH$_2$)$_2$O—Me | H | |
| 641 | OMe | Cl | NMe$_2$ | CO$_2$Me | |
| 642 | OMe | Cl | N(Me)Et | CO$_2$Me | |
| 643 | OMe | Cl | N(Me)-n-Pr | CO$_2$Me | |
| 644 | OMe | Cl | N(Me)All | CO$_2$Me | |
| 645 | OMe | Cl | N(Me)(CH$_2$)$_2$O—Me | CO$_2$Me | |
| 646 | OMe | Cl | NMe$_2$ | CO$_2$Et | |
| 647 | OMe | Cl | N(Me)Et | CO$_2$Et | |
| 648 | OMe | Cl | N(Me)-n-Pr | CO$_2$Et | |
| 649 | OMe | Cl | N(Me)All | CO$_2$Et | |
| 650 | OMe | Cl | N(Me)(CH$_2$)$_2$O—Me | CO$_2$Et | |

B. FORMULATION EXAMPLES a) A dust is obtained by mixing 10 parts by weight of a compound of the formula (I) and/or its salts and 90 parts by weight of talc as inert substance and comminuting the mixture in a hammer mill.

b) A wettable powder which is readily dispersible in water is obtained by mixing 25 parts by weight of a compound of the formula (I) and/or its salts, 64 parts by weight of kaolin-containing quartz as inert substance, 10 parts by weight of potassium lignosulfonate and 1 part by weight of sodium oleoylmethyltaurinate as wetter and dispersant, and grinding the mixture in a pinned-disk mill.

c) A dispersion concentrate which is readily dispersible in water is obtained by mixing 20 parts by weight of a compound of the formula (I) and/or its salts with 6 parts by weight of alkylphenol polyglycol ether (®Triton X 207), 3 parts by weight of isotridecanol polyglycol ether (8 EO) and 71 parts by weight of paraffinic mineral oil (boiling range for example approximately 255 up to over 277° C.) and grinding the mixture in a bowl mill to a fineness of below 5 microns.

d) An emulsifiable concentrate is obtained from 15 parts by weight of a compound of the formula (I) and/or its salts, 75 parts by weight of cyclohexanone as solvent and 10 parts by weight of oxethylated nonylphenol as emulsifier.

e) Water-dispersible granules are obtained by mixing
   75 parts by weight of a compound of the formula (I) and/or its salts,
   10 parts by weight of calcium lignosulfonate,
   5 parts by weight of sodium lauryl sulfate, 3 parts by weight of polyvinyl alcohol and 7 parts by weight of kaolin, grinding the mixture in a pinned-disk mill and granulating the powder in a fluidized bed by spraying on water as granulation liquid.

f) Water-dispersible granules are also obtained by homogenizing and precomminuting, in a colloid mill, 25 parts by weight of a compound of the formula (I) and/or its salts, 5 parts by weight of sodium 2,2'-dinaphthylmethane-6,6'-disulfonate, 2 parts by weight of sodium oleoylmethyltaurinate, 1 part by weight of polyvinyl alcohol, 17 parts by weight of calcium carbonate and 50 parts by weight of water subsequently grinding the mixture in a bead mill, and atomizing and drying the resulting suspension in a spray tower by means of a single-substance nozzle.

C. BIOLOGICAL EXAMPLES

1. Herbicidal Pre-Emergence Effect Against Harmful Plants

Seeds of monocotyledonous or dicotyledonous weeds or crop plants are placed in sandy loam soil in wood-fiber pots and covered with soil. The compounds according to the invention, formulated in the form of wettable powders (WP) or emulsion concentrates (EC), are then applied to the surface of the soil cover in the form of an aqueous suspension or emulsion at a water application rate of 600 to 800 l/ha (converted), with addition of 0.2% wetter. After the treatment, the pots are placed in the greenhouse and kept under good growth conditions for the test plants. The damage to the test plants is scored visually in comparison with untreated controls after an experimental time of 3 weeks has elapsed (herbicidal activity in percent (%): 100% activity=plants have died, 0% activity=like control plants). In this context, for example the compounds Nos. 543, 564, 616 and 621 show in each case at least 90% activity against *Abutilon theophrasti, Amaranthus retroflexus* and *Echinochloa crus* galli at an application rate of 320 g/ha. Compounds Nos. 4 and 564 show in each case at least 90% activity against *Setaria viridis* and *Stellaria media* at an application rate of 320 g/ha.

2. Herbicidal Post-Emergence Activity Against Harmful Plants

Seeds of monocotyledonous or dicotyledonous weeds or crop plants are placed in sandy loam soil in wood-fiber pots, covered with soil and grown in the greenhouse under good growth conditions. 2 to 3 weeks after sowing, the test plants are treated in the one-leaf stage. The compounds according to the invention, formulated in the form of wettable powders (WP) or emulsion concentrates (EC), are then sprayed on to the green plant parts in the form of an aqueous suspension or emulsion at a water application rate of 600 to 800 l/ha (converted), with addition of 0.2% wetter. After the test plants have been left to stand under optimal growth conditions in the greenhouse for approximately 3 weeks, the activity of the preparations is scored visually in comparison with untreated controls (herbicidal activity in percent (%): 100% activity=plants have died, 0% activity=like control plants). In this context, for example the compounds Nos. 4 and 564 show in each case at least 80% activity against *Setaria viridis, Stellaria media* and *Viola tricolor* at an application rate of 80 g/ha. Compounds Nos. 616 and 621 show in each case at least 90% activity against *Abutilon theophrasti, Amaranthus retroflexus* and *Echinochloa crus* galli at an application rate of 80 g/ha.

We claim:

1. A 4-(3-aminobenzoyl)-5-cyclopropylisoxazole of the formula (I) and/or a salt thereof

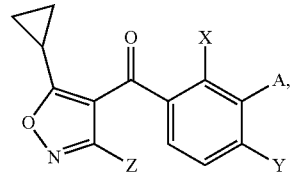

wherein

A is $NR^1R^2$ or $N=CR^3NR^4R^5$, $R^1$ and $R^2$ independently of one another are hydrogen, $(C_1-C_6)$-alkyl, $(C_1-C_4)$-alkoxy-$(C_1-C_6)$-alkyl, $(C_2-C_6)$-alkenyl, $(C_3-C_6)$-cycloalkyl or $(C_3-C_6)$-cycloalkyl-$(C_1-C_6)$-alkyl, $R^3$, $R^4$ and $R^5$ independently of one another are hydrogen or $(C_1-C_6)$-alkyl, X and Y independently of one another are methyl, methoxy, trifluoromethyl, chlorine, bromine, fluorine or methylsulfonyl, Z is hydrogen or $CO_2R^6$, $R^6$ is methyl or ethyl.

2. A 4-(3-aminobenzoyl)-5-cyclopropylisoxazole as claimed in claim 1, wherein A is $NR^1R^2$ or $N=CR^3NR^4R^5$, $R^1$ and $R^2$ independently of one another are hydrogen, methyl, ethyl, propyl, methoxyethyl, ethoxyethyl or methoxypropyl, $R^3$, $R^4$, $R^5$ independently of one another are hydrogen or methyl, X and Y independently of one another are methyl, methoxy, trifluoromethyl, chlorine, bromine, fluorine or methylsulfonyl, Z is hydrogen or $CO_2R^6$, and $R^6$ is methyl or ethyl.

3. A 4-(3-aminobenzoyl)-5-cyclopropylisoxazole of the formula (I) and/or a salt as claimed in claim 1, wherein A is $NR^1R^2$.

4. A 4-(3-aminobenzoyl)-5-cyclopropylisoxazole of the formula (I) and/or a salt as claimed in claim 1, wherein A is $N=CR^3NR^4R^5$.

5. A 4-(3-aminobenzoyl)-5-cyclopropylisoxazole of the formula (I) and/or a salt as claimed in claim 1, wherein Z is $CO_2R^6$.

6. A compound of formula (Ia)

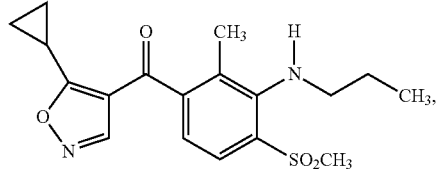

and/or a salt thereof.

7. A herbicidal composition, comprising a herbicidally active content of at least one compound of the formula (I) and/or salt as claimed in claim 1.

8. The herbicidal composition as claimed in claim 7 comprising a mixture with at least one formulation auxiliary.

9. A herbicidal composition as claimed in claim 7 for controlling undesired plants.

10. A composition as claimed in claim 9, wherein the compound of the formula (I) and/or salt is capable of being employed for controlling undesired plants in crops of useful plants.

11. A composition as claimed in claim 10, wherein the useful plants are transgenic useful plants.

12. A herbicidal composition comprising at least one compound of claim 2.

13. A herbicidal composition, comprising a herbicidally active content of at least one compound of formula (Ia) and/or salt as claimed in claim 6.

14. A method of controlling undesired plants, comprising applying an effective amount of at least one compound of the formula (I) and/or salt as claimed in claim 1 to a plant and/or to a location of undesired plant growth.

15. A method for controlling undesired plants comprising applying an effective amount of at least one compound of claim 2 to a plant and/or to a location of undesired plant growth.

16. A method for controlling undesired plants, comprising applying an effective amount of at least one compound of claim 6 to plant and/or to a location of undesired plant growth.

* * * * *